United States Patent
Hirth et al.

(10) Patent No.: US 9,546,161 B2
(45) Date of Patent: Jan. 17, 2017

(54) SYNTHESIS OF UDP-GLUCOSE: N-ACYLSPHINGOSINE GLUCOSYL TRANSFERASE INHIBITORS

(71) Applicant: Genzyme Corporation, Cambridge, MA (US)

(72) Inventors: Bradford H. Hirth, Littleton, MA (US); Craig Siegel, Woburn, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/315,453

(22) Filed: Jun. 26, 2014

(65) Prior Publication Data

US 2015/0148534 A1    May 28, 2015

Related U.S. Application Data

(60) Continuation of application No. 13/420,108, filed on Mar. 14, 2012, now Pat. No. 8,779,163, which is a division of application No. 12/830,962, filed on Jul. 6, 2010, now Pat. No. 8,138,353, which is a continuation of application No. 11/895,632, filed on Aug. 24, 2007, now Pat. No. 7,763,738, which is a division of application No. 10/916,824, filed on Aug. 12, 2004, now Pat. No. 7,265,228, which is a division of application No. 10/197,227, filed on Jul. 16, 2002, now Pat. No. 6,855,830.

(60) Provisional application No. 60/305,814, filed on Jul. 16, 2001.

(51) Int. Cl.
| | |
|---|---|
| C07D 405/06 | (2006.01) |
| C07D 405/10 | (2006.01) |
| C07D 295/185 | (2006.01) |
| C07D 319/18 | (2006.01) |
| C07D 498/04 | (2006.01) |
| A61K 31/4025 | (2006.01) |

(52) U.S. Cl.
CPC ......... *C07D 405/06* (2013.01); *A61K 31/4025* (2013.01); *C07D 295/185* (2013.01); *C07D 319/18* (2013.01); *C07D 498/04* (2013.01)

(58) Field of Classification Search
CPC . C07D 405/06; C07D 405/10; C07D 295/185; C07D 319/18; C07D 498/04
See application file for complete search history.

(56) References Cited

U.S. PATENT DOCUMENTS

| | | |
|---|---|---|
| 4,755,520 A | 7/1988 | Schon et al. |
| 5,387,593 A | 2/1995 | Mattson et al. |
| 5,631,394 A | 5/1997 | Wei et al. |
| 5,684,020 A | 11/1997 | Peglion et al. |
| 5,707,649 A | 1/1998 | Inokuchi et al. |
| 5,763,438 A | 6/1998 | Inokuchi et al. |
| 5,849,326 A | 12/1998 | Inokuchi et al. |
| 5,907,039 A | 5/1999 | Jinbo et al. |
| 5,916,911 A | 6/1999 | Shayman et al. |
| 5,945,442 A | 8/1999 | Shayman et al. |
| 5,952,370 A | 9/1999 | Shayman et al. |
| 5,972,928 A | 10/1999 | Chatterjee |
| 6,030,995 A | 2/2000 | Shayman et al. |
| 6,040,332 A | 3/2000 | Shayman et al. |
| 6,051,598 A | 4/2000 | Shayman et al. |
| 6,228,889 B1 | 5/2001 | Chatterjee |
| 6,255,336 B1 | 7/2001 | Shayman et al. |
| 6,335,444 B1 | 1/2002 | Jinbo et al. |
| 6,511,979 B1 | 1/2003 | Chatterjee |
| 6,569,889 B2 | 5/2003 | Shayman et al. |
| 6,855,830 B2 | 2/2005 | Hirth et al. |
| 6,890,949 B1 | 5/2005 | Shayman et al. |
| 6,916,802 B2 | 7/2005 | Shayman et al. |
| 7,148,251 B2 | 12/2006 | Shayman |
| 7,196,205 B2 | 3/2007 | Siegel et al. |
| 7,253,185 B2 | 8/2007 | Shayman et al. |
| 7,265,228 B2 | 9/2007 | Hirth et al. |
| 7,615,573 B2 | 11/2009 | Siegel et al. |
| 7,763,738 B2 | 7/2010 | Hirth et al. |
| 8,138,353 B2 | 3/2012 | Hirth et al. |
| 8,779,163 B2 | 7/2014 | Hirth et al. |
| 2002/0198240 A1 | 12/2002 | Shayman et al. |
| 2003/0073680 A1 | 4/2003 | Shayman et al. |
| 2004/0260099 A1 | 12/2004 | Shayman |
| 2005/0239862 A1 | 10/2005 | Shayman et al. |
| 2006/0217560 A1 | 9/2006 | Shayman |
| 2007/0072916 A1 | 3/2007 | Shayman |
| 2007/0203223 A1 | 8/2007 | Siegel et al. |

FOREIGN PATENT DOCUMENTS

| | | |
|---|---|---|
| EP | 126974 A1 | 12/1984 |
| EP | 0 765 865 A1 | 4/1997 |
| EP | 1 384 719 A1 | 1/2004 |
| JP | 9-169664 A | 6/1997 |
| JP | 9216856 A | 8/1997 |
| JP | 10324671 A | 12/1998 |
| JP | 10338636 A | 12/1998 |
| WO | WO-97/10817 A1 | 3/1997 |
| WO | WO-98/52553 A1 | 11/1998 |
| WO | WO-01/04108 A1 | 1/2001 |
| WO | WO-02/062777 A2 | 8/2002 |
| WO | WO-03/008399 A1 | 1/2003 |

OTHER PUBLICATIONS

Abdel-Magid, A., et al., "Metal-Assisted Aldol Condensation of Chiral α-Halogenated Imide Enolates: A Stereocontrolled Chiral Epoxide Synthesis," *J. Am. Chem. Soc.*, 108: 4595-4602 (1986).

(Continued)

*Primary Examiner* — Rebecca Anderson
(74) *Attorney, Agent, or Firm* — McCarter & English, LLP; Steven G. Davis; Wei Song

(57) ABSTRACT

Disclosed is a novel enantiomeric synthesis ceramide-like inhibitors of UDP-glucose: N-acylsphingosine glucosyltransferase. Also disclosed are novel intermediates formed during the synthesis.

3 Claims, 4 Drawing Sheets

(56) References Cited

OTHER PUBLICATIONS

Abe, A., et al., "Improved Inhibitors of Glucosylceramide Synthase," J. Biochem., 111: 191-196 (1992).
Abe, A., et al., "Induction of Glucosylceramide Synthase by Synthase Inhibitors and Ceramide," Biochim. Biophys. Acta, 1299: 333-341 (1996).
Abe, A., et al., "Metabolic Effects of Short-Chain Ceramide and Glucosylceramide on Sphingolipids and Protein Kinase C," Eur. J. Biochem., 210: 765-773 (1992).
Abe, A., et al., "Reduction of Globotriasylceramide in Fabry disease mice by substrate deprivation", J. Clin. Invest. 105(11): 1563-1571, Jun. 2000.
Abe, A., et al., "Structural and stereochemical studies of potent inhibitors of glucosylceramide synthase and tumor cell growth," J. of Lipid Research, 36: 611-621 (1995).
Alker, D., et al., "Application of Enantiopure Templated Azomethine Ylids to β-Hydroxy-α-amino Acid Synthesis," Tetrahedron: Asymmetry, 54: 6089-6098 (1998).
Alon, R., et al., "Glycolipid Ligands for Selectins Support Leukocyte Tethering and Rolling Under Physiologic Flow Conditions," J. Immunol., 154: 5356-5366 (1995).
Ames, Bruce N., "Assay of Inorganic Phosphate, Total Phosphate and Phosphatases," Methods Enzymol., 8: 115-118 (1966).
Bielawska, A., et al., "Ceramide-Mediated Biology: Determination of Structural and Stereospecific Requirements Through the Use of N-Acyl-Phenylaminoalcohol Analogs," J. Biol. Chem., 267: 18493-18497 (1992).
Bielawska, A., et al., "Modulation of Cell Growth and Differentiation by Ceramide," FEBS Letters, 307(2): 211-214 (1992).
Blobe, G. C., et al., "Regulation of Protein Kinase C and Role in Cancer Biology," Cancer Metastasis Rev., 13: 411-431 (1994).
Brenkert, A., et al., "Synthesis of Galactosyl Ceramide and Glucosyl Ceramide by Rat Brain: Assay Procedures and Changes with Age," Brain Res., 36: 183-193 (1972).
Carson, K.G., et al., "Studies on Morpholinosphingolipids: Potent Inhibitors of Glucosylceramide Synthase," Tetrahedron Letters, 35(17): 2659-2662 (1994).
Dellaria, Jr., J.F., et al., "Enantioselective Synthesis of α-Amino Acid Derivatives via the Stereoselective Alkylation of a Homochiral Glycine Enolate Synthon," J. Org. Chem., 54: 3916-3926 (1989).
Evans, D. A., et al., "Stereoselective Aldol Condensations Via Boron Enolates," J. Am. Chem. Soc., 103: 3099-3111 (1981).
Felding-Habermann, B., et al., "A Ceramide Analog Inhibits T Cell Proliferative Response Through Inhibition of Glycosphingolipid Synthesis and Enhancement of N, N-Dimethylsphingosine Synthesis," Biochemistry, 29: 6314-6322 (1990).
Gatt, S., et al., "Assay of Enzymes of Lipid Metabolism With Colored and Fluorescent Derivatives of Natural Lipids," Meth. Enzymol., 72: 351-375 (1981).
Hakomori, S., "New Directions in Cancer Therapy Based on Aberrant Expression of Glycosphingolipids: Anti-Adhesion and Ortho-Signaling Therapy," Cancer Cells, 3(12): 461-470 (1991).
Hammett, L. P., Physical Organic Chemistry, (NY: McGraw-Hill), (1940).
Harwood, L.M., et al., "Asymmetric Cycloadditions of Aldehydes to Stabilized Azomethine Ylids: Enantiocontrolled Construction of β-Hydroxy-α-amino acid Derivitives," Tetrahedron: Asymmetry, 3(9): 1127-1130 (1992).
Harwood, L.M., et al., "Double diastereocontrol in the synthesis of enantiomerically pure polyoxamic acid," Chem. Commun., 2641-2642 (1998).
Hospattankar, A. V., et al., "Changes in Liver Lipids After Administration of 2-Decanoylamino-3-Morpholinopropiophenone and Chlorpromazine," Lipids, 17(8): 538-543 (1982).
Högberg, T., et al., "Theoretical and Experimental Methods in Drug Design Applied on Antipsychotic Dopamine Antagonists." In Textbook of Drug Design and Development, pp. 55-91 (1991).
Inokuchi, J., et al., "Antitumor Activity: Via Inhibition of Glycosphingolipid Biosynthesis," Cancer Letters, 38: 23-30 (1987).
Inokuchi, J., et al., "Inhibition of Experimental Metastasis of Murine Lewis Lung Carcinoma by an Inhibitor of Glucosylceramide Synthase and Its Possible Mechanism of Action," Cancer Res., 50: 6731-6737 (1990).
Inokuchi, J., et al., "Preparation of the active isomer of 1-phenyl-2-decanoylamino-3-morpholino-1-propanol, inhibitor of murine glucocerebroside synthetase," J. of Lipid Research, 28: 565-571 (1987).
Jaffrézou, J., et al., "Inhibition of Lysosomal Acid Sphingomyelinase by Agents which Reverse Multidrug Resistance," Biochim. Biophys. Acta, 1266: 1-8 (1995).
Jimbo, M., et al., "Development of a New Inhibitor of Glucosylceramide Synthase", J. Biochem. 127(3), 485-91, (2000).
Kalén, A., et al., "Elevated Ceramide Levels in GH4C1 Cells Treated with Retinoic Acid," Biochim. Biophys. Acta, 1125: 90-96 (1992).
Kopaczyk, K. C., et al., "In Vivo Conversions of Cerebroside and Ceramide in Rat Brain," J. Lipid Res., 6: 140-145 (1965).
Kurosawa, M., et al., "C-Labeling of a Novel Atypical β-Adrenoceptor Agonist, SM-11044," Journal of Labelled Compounds and Radiopharmaceuticals, 38(3): 285-297 (1996).
Lee, L., et al., "Improved Inhibitors of Glucosylceramide Synthase," J. Biol. Chem., 274(21): 14662-14669 (1999).
Mitchell, S.A., et al., "Glycosyltransferase Inhibitors: Synthesis of D-threo-PDMP, L-threo-PDMP, and Other Brain Glucosylceramide Synthase Inhibitors from D- or L-Serine," J. Org. Chem., 63: 8837-8842 (1998).
Miura, T., et al., "Synthesis and Evaluation of Morpholino and Pyrrolidinosphingolipids as Inhibitors of Glucosylceramide Synthase", Bioorganic and Medicinal Chemistry, (6) 1481-1489 (1998).
Nakamura, K., et al., "Coomassie Brilliant Blue Staining of Lipids on Thin-Layer Plates," Anal. Biochem., 142: 406-410 (1984).
Nicolaou, K.C., et al., "A Practical and Enantioselective Synthesis of Glycosphingolipids and Related Compounds. Total Synthesis of Globotriaosylceramide (Gb3)," J. Am. Chem. Soc., 110: 7910-7912 (1988).
Nishida, A., et al., "Practical Synthesis of threo-(1s, 2S)- and erythro-(1 R, 2S)-1-Phenyl-2-palmitoylamino-3-morpholino-1-propanol (PPMP) from L-Serine," Synlett, 389-390 (1998).
Ogawa, S., et al., "Synthesis and Biological Evaluation of Four Stereoisomers of PDMP-Analogue, N-(2-Decylamino-3-Hydroxy-3-Phenylprop-1-YL)-β-Valienamine, and Related Compounds," Bioorganic & Medicinal Chemistry Letters, 7(14):1915-1920 (1997).
Preiss, J., et al., "Quantitative Measurement of sn-1,2-Diacylglycerols Present in Platelets, Hepatocytes, and ras- and sis-Transformed Normal Rat Kidney Cells," J. Biol. Chem., 261(19): 8597-8600 (1986).
Radin, N. S., "Killing Cancer Cells by Poly-drug Elevation of Ceramide Levels, A Hypothesis Whose Time Has Come?," Eur. J. Biochem. 268(2): 193-204 (2001).
Radin, N. S., et al., "Metabolic Effects of Inhibiting Glucosylceramide Synthesis with PDMP and Other Substances." In Advances in Lipid Research; Sphingolipids, Part B., R. M. Bell et al., Eds. (San Deigo: Academic Press), 26: 183-213 (1993).
Radin, N. S., et al., "Ultrasonic Baths as Substitutes for Shaking Incubator Baths," Enzyme, 45: 67-70 (1991).
Radin, N. S., et al., "Use of an Inhibitor of Glucosylceramide Synthesis, D-1-Phenyl-2-decanoylamino-3-morpholino-1-propanol," In NeuroProtocols: A Companion to Methods in Neurosciences, S. K. Fisher et al., Eds., (San Diego: Academic Press) 3: 145-155 (1993).
Rosenwald, A. G., et al., "Effects of a Sphingolipid Synthesis Inhibitor on Membrane Transport Through the Secretory Pathway," Biochemistry, 31: 3581-3590 (1992).
Rosenwald, A. G., et al., "Effects of the Glucosphingolipid Synthesis Inhibitor, PDMP, on Lysosomes in Cultured Cells," J. Lipid Res., 35: 1232-1240 (1994).
Shayman, J. A., et al., "Glucosphingolipid Dependence of Hormone-Stimulated Inositol Trisphosphate Formation," J. Biol. Chem., 265(21): 12135-12138 (1990).

(56) References Cited

OTHER PUBLICATIONS

Shayman, J. A., et al., "Modulation of Renal Epithelial Cell Growth by Glucosylceramide: Association with Protein Kinase C, Sphingosine, and Diacylglycerol," J. Biol. Chem., 266(34): 22968-22974 (1991).

Shukla, A., et al., "Metabolism of D-[$^3$H]threo-1-phenyl-2-decanoylamino-3-morpholino-1-propanol, an inhibitor of glucosylceramide synthesis and the synergistic action of an inhibitor of microsomal momooxygenase," J. of Lipid Research, 32:713-722 (1991).

Shukla, G. S., et al., "Glucosylceramide Synthase of Mouse Kidney: Further Characterization with an Improved Assay Method," Arch. Biochem. Biophys., 283(2): 372-378 (1990).

Shukla, G., et al., "Rapid Kidney Changes Resulting From Glycosphingolipid Depletion by Treatment with a Glucosyltransferase Inhibitor," Biochim. Biophys. Acta, 1083: 101-108 (1991).

Skehan, P., et al., "New Colorimetric Cytotoxicity Assay for Anti-cancer-Drug Screening," J. Natl. Cancer Inst., 82(13): 1107-1112 (1990).

Strum, J. C., et al., "1-β-D-Arabinofuranosylcytosine Stimulates Ceramide and Diglyceride Formation in HL-60 Cells," J. Biol. Chem., 269(22): 15493-15497 (1994).

Svensson, M., et al., "Epithelial Glucosphingolipid Expression as a Determinant of Bacterial Adherence and Cytokine Production," Infect. Immun., 62(10): 4404-4410 (1994).

Tang, W., et al., "Phorbol Ester Inhibits 13-Cis-Retinoic Acid-Induced Hydrolysis of Phosphatidylinositol 4,5-Biophosphate in Cultured Murine Keratinocytes: A Possible Negative Feedback Via Protein Kinase C-Activation," Cell Bioch. Funct., 9: 183-191 (1991).

Uemura, K., et al., "Effect of an Inhibitor of Glucosylceramide Synthesis on Cultured Rabbit Skin Fibroblasts," J. Biochem., (Tokyo) 108(4): 525-530 (1990).

Vunnam, R.R., et al., "Analogs of Ceramide That Inhibit Glucocerebroside Synthetase in Mouse Brain," Chemistry and Physics of Lipids, L.D. Bergelson, et al., eds. (Elsevier/North-Holland Scientific Publishers Ltd.), 26: 265-278 (1980).

Wong, C-H., et al., "Synthesis and Evaluation of Homoazasugars as Glycosidase Inhibitors," J. Org. Chem., 60: 1492-1501, (1995).

Zador, I. Z., et al., "A Role for Glycosphingolipid Accumulation in the Renal Hypertrophy of Streptozotocin-Induced Diabetes Mellitus," J. Clin. Invest., 91: 797-803 (1993).

Ziche, M., et al., "Angiogenesis Can be Stimulated or Repressed in In Vivo by a Change in GM3:GD3 Ganglioside Ratio," Lab. Invest., 67(6): 711-715 (1992).

John McMurry, translated by Mitsuaki Kodama et al., Organic Chemistry, vol. 1, 3rd ed., Tokyo Kagaku Dojin Co., Ltd, Feb. 10, 1994, p. 274-279.

S. Warren, translated by Yujirou Nomura, Program Learning Organic Synthetic Chemistry, Kodansha Ltd, Dec. 10, 1979, pp. xvi-xix.

Hiroshi Takahashi, Organic Synthesis of Targeted Compounds, Sankyo Shuppan Co., Ltd., May 20, 1981, p. 6-7.

Compound 5

Compound 6

Compound 7

Compound 8

SYNTHESIS OF UDP-GLUCOSE: N-ACYLSPHINGOSINE GLUCOSYL TRANSFERASE INHIBITORS

RELATED APPLICATIONS

This application is a continuation of U.S. patent application Ser. No. 13/420,108, filed Mar. 14, 2012, which is a divisional of U.S. patent application Ser. No. 12/830,962, filed Jul. 6, 2010 and now U.S. Pat. No. 8,138,353, which, in turn, is a continuation of U.S. patent application Ser. No. 11/895,632, filed Aug. 24, 2007 and now U.S. Pat. No. 7,763,738, which, in turn, is a divisional of U.S. patent application Ser. No. 10/916,824, filed Aug. 12, 2004 and now U.S. Pat. No. 7,265,228, which, in turn, is a divisional of U.S. patent application Ser. No. 10/197,227, filed Jul. 16, 2002 and now U.S. Pat. No. 6,855,830, which, in turn, claims the benefit of U.S. Provisional Application No. 60/305,814, filed Jul. 16, 2001. The entire contents of each of the aforementioned applications are incorporated herein by reference.

BACKGROUND OF THE INVENTION

Glycosphingolipids (GSLs) are a class of naturally occurring compounds which have a multitude of biological functions, including the ability to promote cell growth, cell differentiation, adhesion between cells or between cells and matrix proteins, binding of microorganisms and viruses to cells, and metastasis of tumor cells. GSLs are derived from glucosylceramide (GlcCer), which is produced from ceramide and UDP-glucose by the enzyme UDP-glucose: N-acylsphingosine glucosyltransferase (GlcCer synthase). The structure of ceramide is shown below:

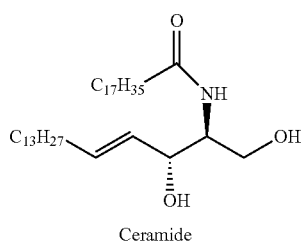

Ceramide

The accumulation of GSLs has been linked to a number of diseases, including Tay-Sachs, Gaucher's, and Fabry's diseases (see, for example, U.S. Pat. No. 6,051,598). GSLs have also been linked to certain cancers. For example, it has been found that certain GSLs occur only in tumors or at abnormally high concentrations in tumors; exert marked stimulatory or inhibitory actions on tumor growth when added to tumor cells in culture media; and inhibit the body's normal immunodefense system when shed by tumors into the surrounding extracellular fluid. The composition of a tumor's GSLs changes as the tumors become increasingly malignant and antibodies to certain GSLs inhibit the growth of tumors.

Compounds which inhibit GlcCer synthase can lower GSL concentrations and have been reported to be useful for treating a subject with one of the aforementioned diseases. A number of potent inhibitors of GlcCer, referred to herein as "amino ceramide-like compounds", are disclosed in U.S. Pat. Nos. 6,051,598, 5,952,370, 5,945,442, 5,916,911 and 6,030,995. The term "ceramide-like compounds" refers to analogs of ceramide in which: 1) the primary alcohol is replaced with a substituted amino group; and 2) the alkenyl group is replaced with an aryl group, preferably phenyl or substituted phenyl. The corresponding N-deacylated compounds are referred to as "sphingosine-like compounds."

Unfortunately, known methods of preparing amino ceramide-like compounds are poorly suited for manufacturing on an industrial scale. Because of the two chiral centers, most known syntheses generate four diastereoisomers, resulting in the need to separate diastereomers by chromatography and to isolate the desired enantiomer by crystallization after derivitization with optically active reagents, e.g., dibenzoyltartaric acid isomers (see, for example, Inokuchi and Radin, *Journal of Lipid Research* 28:565 (1987)). Neither of the processes are amenable to large scale preparations. Enantioselective synthesis of amino ceramide-like compounds using diastereoselective reductions have been reported (Mitchell, et al., *J. Org. Chem.* 63:8837 (1998) and Nishida, et al., *SYNLETT* 1998:389 (1998)), but require over ten steps, some of which utilized expensive reagents such as diisobutylaluminum hydride (DIABAL) and Garner Aldehyde (tert-butyl (R)-(+)-4 formyl-2,2-dimethyl-3-oxazolidine carboxylate). Thus, there is a critical need for enantioselective syntheses of amino ceramide-like compounds which are more economical and efficient, and involve fewer steps than known syntheses.

SUMMARY OF THE INVENTION

Provided herein is an efficient, highly enantioselective synthesis of amino ceramide-like compounds. This synthesis of amino ceramide-like compounds involves only five steps from known compounds. For example, the ceramide-like compound designated as "Compound 5" in FIG. 2 was produced in an enantiomeric excess of at least 99.6% and an overall yield of 9% (see Examples 1 and 2). Novel intermediates prepared during the course of the synthesis are also disclosed.

The present invention is directed is a method of preparing a ceramide-like compound represented by Structural Formula (I):

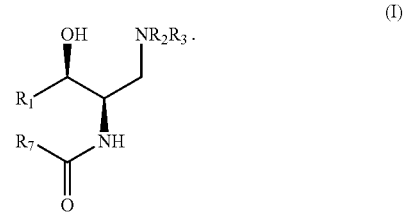

$R_1$ is a substituted or unsubstituted aromatic group; preferably, $R_1$ is a substituted or unsubstituted phenyl group, more preferably phenyl substituted in the meta/para positions with —$OCH_2O$—, —$OCH_2CH_2O$— or in the para position with halo, lower alkyl thiol, —OH, —O(phenyl), —$OCH_2$(phenyl), lower alkyl, amino, lower alkyl amino, lower dialkyl amino, or —O(lower alkyl);

$R_2$ and $R_3$ are independently —H, a substituted or unsubstituted aliphatic group or, taken together with the nitrogen atom to which they are bonded, are a substituted or unsubstituted non-aromatic heterocyclic ring.

$R_7$ is a substituted or unsubstituted aliphatic group, preferably a C1-C30 straight chain unsubstituted aliphatic group or a C1-C30 straight chained aliphatic group substituted with one or more C1-C2 alkyl groups, more preferably an unsubstituted C1-C30 straight chain alkyl or alkenyl group and even more preferably an unsubstituted C7-C10 or C10-C16 straight chain alkyl or alkenyl group.

The method of preparing a ceramide-like compound represented by Structural Formula (I) comprises a first step whereby an amine compound $HNR_2R_3$ is reacted, with a cyclic starting material represented by Structural Formula (II):

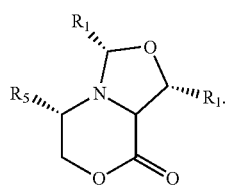

(II)

The reaction between the amine compound $HNR_2R_3$ and the cyclic starting material represented by Structural Formula (II) forms an amide intermediate represented by Structural Formula (III):

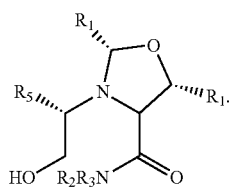

(III)

In Structural Formulas (II) and (III), $R_1$-$R_3$ are as described for Structural Formula (I); and $R_5$ is a substituted or unsubstituted aromatic group, preferably a substituted or unsubstituted phenyl group.

The method of preparing a ceramide-like compound represented by Structural Formula (I) comprises a second step whereby the amino acetal group in the intermediate represented by Structural Formula (III) is hydrolyzed to form the acyclic compound represented by Structural Formula (IV).

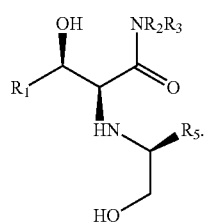

(IV)

$R_1$, $R_2$, $R_3$ and $R_5$ in Structural Formulas (IV) are as defined in Structural Formulas (I)-(III).

The method of preparing a ceramide-like compound represented by Structural Formula (I) comprises a third step whereby the acyclic precursor compound represented by Structural Formula (IV) is reacted with an amide reducing agent to form a compound represented by Structural Formula (V):

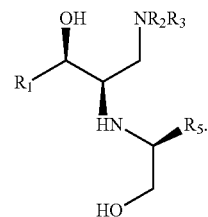

(V)

$R_1$, $R_2$, $R_3$ and $R_5$ in Structural Formula (V) are as defined in Structural Formulas (I)-(IV).

The method of preparing a ceramide-like compound represented by Structural Formula (I) comprises a fourth step whereby the —NHCH(—CH$_2$OH)R$_5$ group of the amine compound represented by Structural Formula (V) is debenzylated to form a sphingosine-like compound represented by Structural Formula (VI):

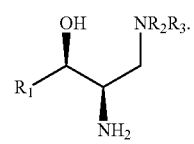

(VI)

Preferably, the debenzylation is achieved by hydrogenation. $R_1$, $R_2$ and $R_3$ are as described for Structural Formulas (I)-(V).

The method of preparing a ceramide-like compound represented by Structural Formula (I) comprises a fifth step whereby the sphingosine-like compound represented by Structural Formula (VI) is acylated to form the ceramide-like compound represented by Structural Formula (I).

Other embodiments of the present invention include each of the individual reactions described above, taken separately and in combination with the other reactions.

Other embodiments of the present invention are intermediates in the preparation of the ceramide-like compound represented by Structural Formula (I) by the methods disclosed herein. In one example, the present invention is directed to an intermediate represented by Structural Formula (VII):

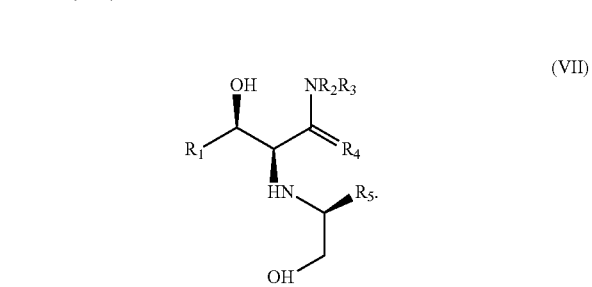

(VII)

$R_1$-$R_3$ and $R_5$ are as described above for Structural Formulas (I)-(VI); and $R_4$ is $H_2$ or O.

In another embodiment, the present invention is directed to an intermediate represented by Structural Formula (VIII):

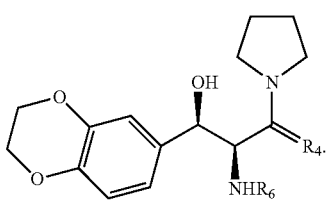

(VIII)

$R_4$ is $H_2$ or O; and
$R_6$ is represented by Structural Formula (IX):

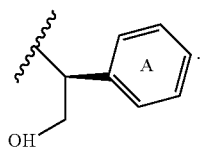

(IX)

Phenyl ring A in Structural Formula (IX) is substituted or unsubstituted. Preferably, however, phenyl ring A is unsubstituted. Alternatively, $R_4$ in Structural Formula (VIII) is $H_2$ and $R_6$ is —H.

In another embodiment, the present invention is directed to an intermediate represented by Structural Formula (X):

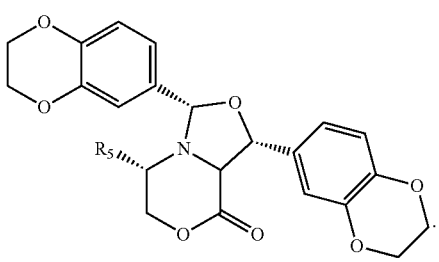

(X)

$R_5$ in Structural Formula (X) is as defined for Structural Formula (I).

The methods of the present invention can be utilized to prepare ceramide-like compounds that inhibit the enzyme GlcCer synthase in five steps from known starting materials. The synthesis is highly efficient, resulting in an overall yield that is generally greater than 8% and in an enantiomeric excess that is typically greater than 99%. The synthesis utilizes inexpensive reagents and therefore provides an economical route to potent inhibitors of GlcCer synthase.

DETAILED DESCRIPTION OF THE INVENTION

Figure 1:
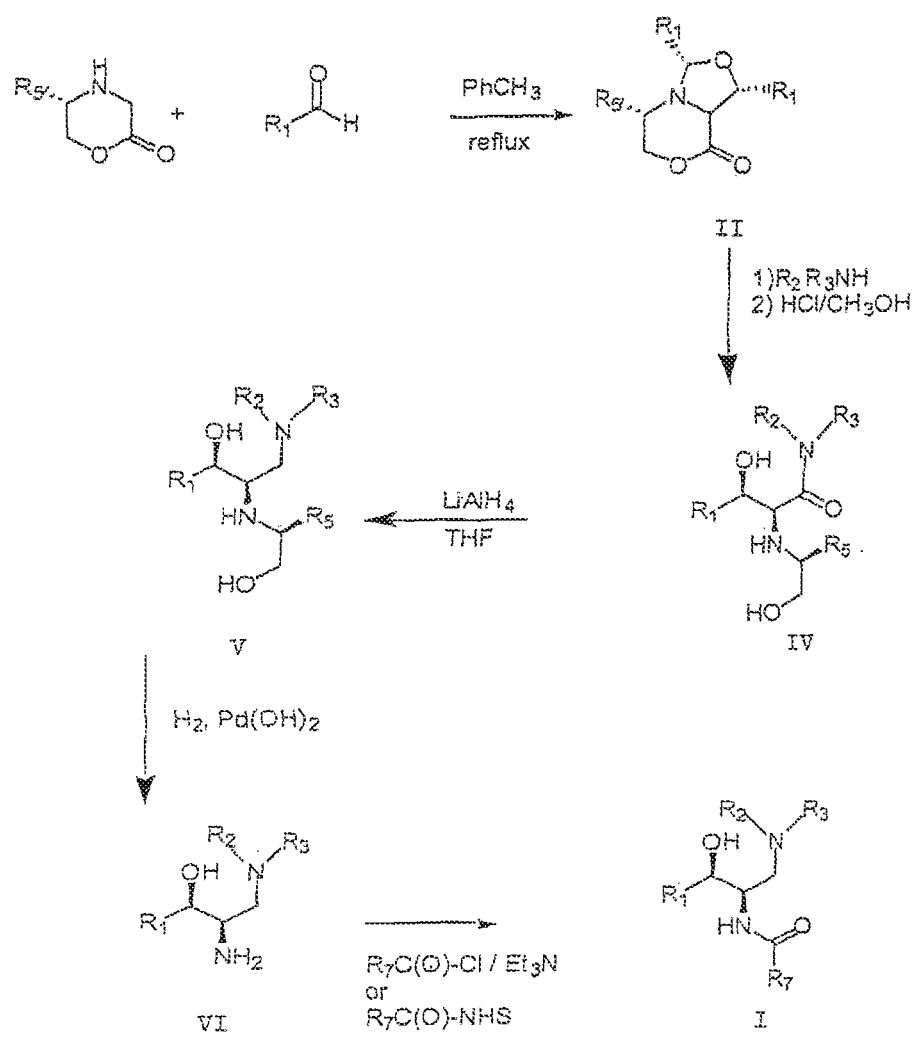
FIG. 1 is a schematic showing the synthesis of ceramide-like compounds represented by Structural Formula (I) using the methods and intermediates disclosed herein.
Figure 2:
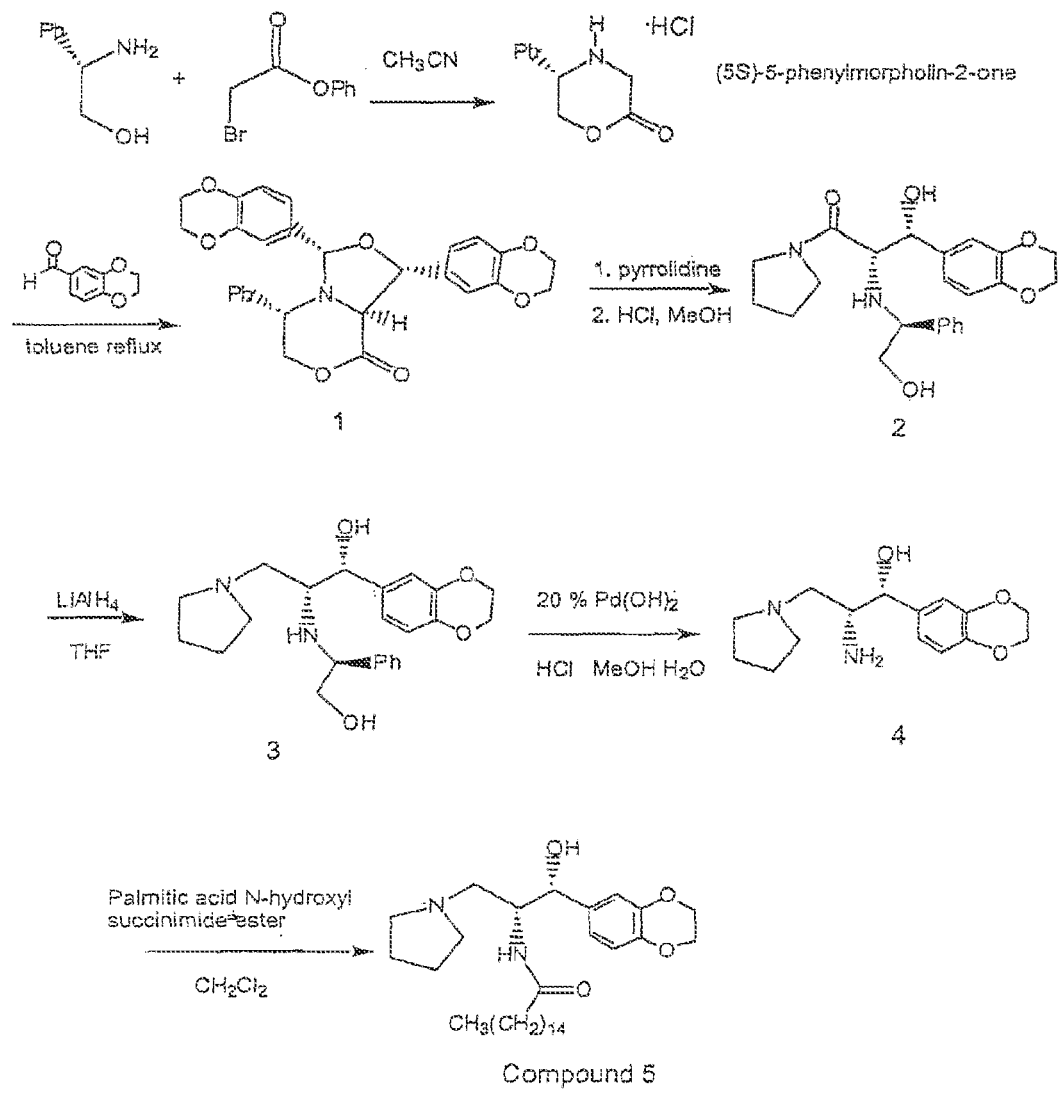
FIG. 2 is a schematic showing the synthesis of ceramide-like Compound (5) using the methods disclosed herein.
Figure 3:
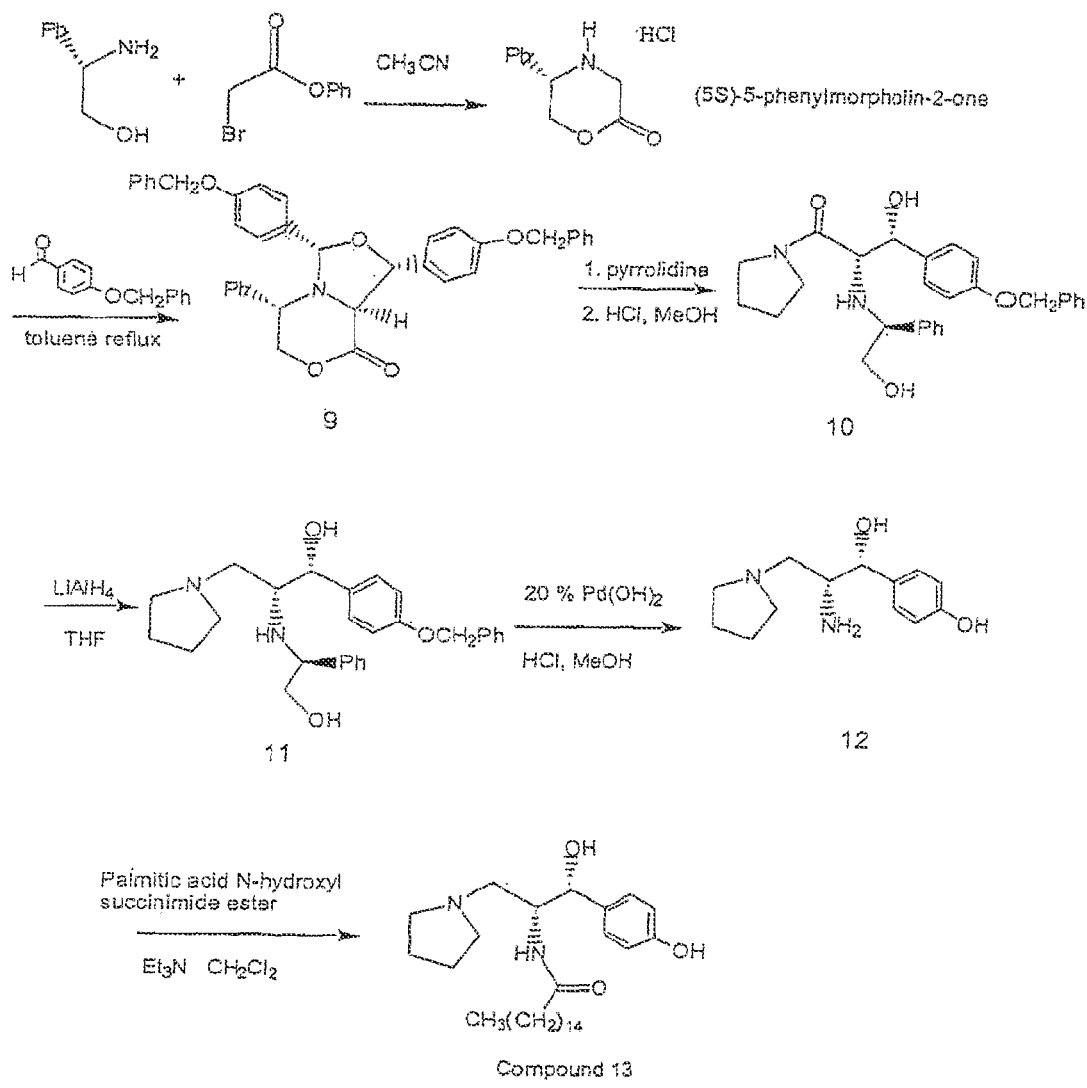
FIG. 3 is a schematic showing the synthesis of ceramide-like compound (13) using the methods disclosed herein.
Figure 4:
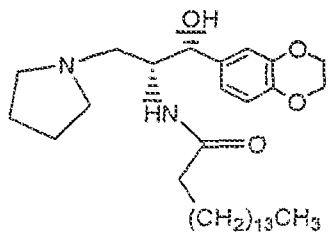
FIG. 4 shows the structures of Compounds (5)-(8).
Figure 4:
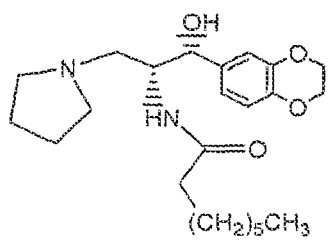
Figure 4:
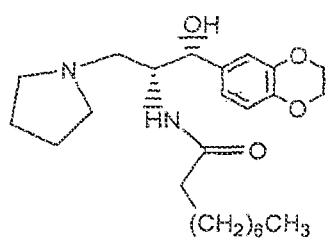
Figure 4:
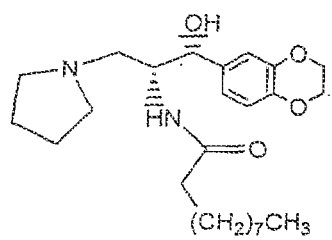

Described herein is a five step synthesis of amino ceramide-like compounds from known starting materials. The synthesis begins with the preparation of the cyclic starting material represented by Structural Formula (II). The cyclic starting material is reacted with a suitable amine, thereby opening the lactone ring and forming the amide intermediate represented by Structural Formula (III). The amino acetal in the amide intermediate is hydrolyzed to form the acyclic compound represented by Structural Formula (IV). The amide of this acyclic compound is reduced with an amide reducing agent to form an amine compound represented by Structural Formula (V), which is in turn debenzylated to form the sphingosine-like compound represented by Structural Formula (VI). The primary amine of the sphingosine-like compound represented by Structural Formula (VI) can then be acylated to form an amino ceramide-like compound. This synthesis is shown schematically in FIG. 1. A detailed description of each reaction in the synthesis is provided below.

The cyclic starting material represented by Structural Formula (II) is prepared according to methods described in Alker, et al., *Tetrahedron* 54:6089 (1998) and Harwood and Robertson, *Chem. Commun.* 1998:2641 (1998). Specifically, (5S)-5-phenylmorpholin-2-one is reacted with at least two equivalents and preferably from about 2.5 to about 5.0 equivalents of aryl aldehyde $R_1$CHO under dehydrating conditions. $R_1$ is as defined in Structural Formula (I). "Dehydrating conditions" refer to conditions under which water is removed from the reaction mixture. Removal of water can be achieved, for example, by carrying out the reaction in presence of a reagent (a "dehydrating reagent") that reacts with water (e.g., molecular sieves) but is substantially inert towards the other reagents present in the reaction mixture, or removal of water can also be achieved by azeotroping with a solvent such as toluene. Sufficient dehydrating reagent is used to remove the two equivalents of water (relative to cyclic starting material) released during the reaction. The concentration of reagents if typically between about 0.01 M and about 5.0 M, more typically between about 0.1 M and about 1.0 M; suitable reaction temperatures range between about 50° C. and about 150° C., preferably between about 100° C. and about 120° C.

The cyclic starting material is converted to the amide intermediate represented by Structural Formula (II) by reacting the cyclic starting material with the amine $NHR_2R_3$ under conditions suitable for amidating an ester with an amine. Such conditions are well known in the art and are described, for example, in March, "Advanced Organic Chemistry—Reactions, Mechanisms and Structure", Third Edition, John Wiley & Sons, 1985, pages 375-76, and references cited therein. Although an excess of either reagent can be used, cyclic starting material is more commonly the limiting reagent. Generally up to about fifteen equivalents of amine relative to cyclic starting material are used, typically up to about eight equivalents. The reaction can be done neat, however, it is more usually carried out in a aprotic, non-nucleophilic solvent at amine concentrations as dilute as 0.01 M. Amine concentrations are more typically, however, between about 0.4 M and about 4.0 M. Suitable solvents include halogenated solvents such as chloroform, dichloromethane and 1,2-dichloroethane, acetonitrile, dimethylformamide (DMF), ethereal solvents such as diethyl ether, tetrahydrofuran (THF) and 1,4-dioxane and aromatic solvents such as benzene and toluene. Suitable reaction temperatures generally range from about 0° C. to about 100° C., typically between about 25° C. to about 35° C.

Conditions for hydrolyzing aminoacetals are known in the art and are described, for example, in March, "Advanced Organic Chemistry—Reactions, Mechanisms and Structure", Third Edition, John Wiley & Sons, 1985, pages 329-32, and references cited therein. For example, the aminoacetal group in the amide intermediate represented by Structural Formula (III) can be hydrolyzed with dilute aqueous mineral acid. Suitable acids include hydrochloric acid, sulfuric acid or phosphoric acid, although hydrochloric is the most common choice. Organic acids such as acetic acid and sulfonic acids (e.g., methansulfonic acid, toluenesulfonic acid, trifluormethylsulfonic acid and the like) can also be used. At least one equivalent of acid relative to the intermediate is typically used, but an excess of acid is preferred to ensure complete hydrolysis, for example, excesses of at least ten fold, preferably an excess of about two to about three fold and more preferably between about 10-50%. The concentration of acid in the reaction mixture is generally between about 0.05 M to about 1.0 M, typically between about 0.1 M and about 0.5 M. An organic co-solvent miscible with water is often used to solubilize the intermediate. Examples include alcohols such as methanol or ethanol and DMF. Common solvent ratios of organic solvent to water range between about 1:1 to about 8:1. Suitable reaction temperatures range from ambient temperature to about 100° C., preferably between about 60° C. to about 80° C. Alternatively, the amino acetal can be hydrolyzed with Lewis acids such as trimethylsilyl iodide, wet silica gel or $LiBF_4$ in wet acetonitrile, as described in March, supra.

An "amide reducing agent" is a reagent which can reduce an amide to an amine. Such reagents are known in the art and are disclosed in, for example, in March, "Advanced Organic Chemistry—Reactions, Mechanisms and Structure", Third Edition, John Wiley & Sons, 1985, pages 1099-1100, Brown and Krishnamurthy, *Aldrichimica Acta* 12:3 (1979) and references cited therein. Examples include lithium aluminum hydride, lithium triethyl borohydride, borane reagents (e.g., borane●tetrahydrofuran, borane●methyl sulfide, disiamylborane, and the like), aluminum hydride, lithium trimethoxy aluminum hydride and triethyloxonium fluoroborate/sodium borohydride. In the method of the present invention, lithium aluminum hydride is the most commonly used amide reducing agent. Although as little as 0.5 equivalents of lithium aluminum hydride relative to amide starting material can be used, it is more common to use an excess, often up to about five equivalents. Preferably, between about 1.5 and about 2.5 equivalents of lithium aluminum hydride are used relative to amine starting material. Ethereal solvents are typically used for the reduction; examples include diethyl ether, THF, glyme, diglyme and 1,4-dioxane. Suitable concentrations of reducing agent are generally between about 0.1 M and about 5.0 M, more typically between about 0.8 M and about 1.5 M. The reduction is most commonly carried out at ambient temperature, but temperatures between about 0° C. and about 80° C. or 100° C. can also be used.

To form the sphingosine-like compound represented by Structural Formula (VI), the amine compound represented by Structural Formula (V) is debenzylated. The term "debenzylating" is used herein to refer to cleaving the carbon-nitrogen bond of a group —NH—$CH_2$Z, wherein Z is an aryl group, preferably phenyl. Optionally, the methylene group can be replaced with a methine group. With respect to the sphingosine-like compound represented by Structural Formula (VI), "debenzylation" refers to converting the —NHCH(—$CH_2$OH)$R_5$ group to —$NH_2$. Debenzylation conditions are well known in the art and are disclosed, for example, in Greene and Wuts, "Protective Groups in Organic Synthesis", John Wiley & Sons (1991), pages 384-86 and references cited therein.

Preferably, debenzylation is achieved by hydrogenation under a hydrogen atmosphere and in the presence of a hydrogenation catalyst. Suitable hydrogen pressures are generally between about atmospheric pressure and about 1000 pounds per square inch. Other sources of hydrogen (e.g., formic acid, ammonium formate, cyclohexene and the like) can also be used. Suitable hydrogenation catalysts include 20% palladium hydroxide on carbon (Perlman's catalyst), palladium chloride, palladium, platinum oxide and palladium on carbon. Typically, between about 10% and about 100% weight/weigh (w/w) relative to amine compound is used. In most instances, an organic acid such as formic acid, acetic acid or trifluoroacetic acid or an inorganic acid such as hydrochloric acid or sulfuric acid is present, for example, between about one to about five equivalents relative to amine compound, preferably between about 1.6 to about 2.4 equivalents. The reaction is most commonly carried out in an alcoholic solvent such as methanol or ethanol with water as co-solvent (e.g., between 0% and about 50% volume/volume (v/v), preferably between about 5% and about 15% v/v). Reaction temperatures between about 0° C. and about 50° C. are suitable, preferably between about 25° C. and about 40° C.

Many debenzylation conditions other than hydrogenation are known in the art and are included in the present invention. Examples include sodium metal and $NH_3$ (see, for example, du Vigneaud and Behrens, *J. Biol. Chem.* 117:27 (1937)), $CCl_3CH_2OCOCl$, $CH_3CN$ (see, for example, Rawal, et al., *J. Org. Chem.,* 52:19 (1987)), $Me_3SiCH_2CH_2OCOCl$, THF, −50° C., then 25° C. overnight (see, for example, Campbell, et al., *Tetrahedron Lett.,* 28:2331 (1987)), α-chloroethyl chloroformate and sodium hydroxide (see, for example Olofson, et al., *J. Org. Chem.* 49:2081 (1984) and DeShong and Kell, *Tetrahedron Lett.,* 27:3979 (1986)), vinyl chloroformate (see, for example, Olofson et al., *Tetrahedron Lett.,* 1977:1567 (1977) and Cooley and Evain, *Synthesis,* 1989:1 (1989)), $RuO_4$, $NH_3$, $H_2O$ (see, for example, Gao and Jones, *J. Am. Chem. Soc.,* 109:1275 (1987)) and m-chloroperoxybenzoic acid followed by $FeCl_2$-10° C. (see, for example, Monkovic, et al., *Synthesis,* 1985:770 (1985).

The sphingosine-like compound represented by Structural Formula (VI) is converted to a ceramide-like compound by acylating the free amine. Acylations of amine groups are well known in the art and can be carried out, for example, by reacting the amine with an acylating agent $R_7C(O)$—X. $R_7$ is as described above for Structural Formula (I) and X is a leaving group that is readily displaced by a primary amine. Conditions for this reaction are described in, for example, in March, "Advanced Organic Chemistry—Reactions, Mechanisms and Structure", Third Edition, John Wiley & Sons, 1985 and references cited therein. Examples of suitable acylating agents include acid halides, anhydrides or esters. Preferably, the amine is acylated with an acid chloride. Generally, equimolar amounts of the sphingosine-like compound and the acid chloride are used in the presence of a small excess, relative to the acid chloride, of a tertiary amine such as triethylamine, diisopropylethylamine, dimethylaminopyridine or pyridine is used. However, an excess of acid chloride (typically about 10-50%) can be used when the sphingosine-like compound is limiting, and vice versa. The concentrations of the reagents in the reaction mixture normally vary between about 0.005 M and about 5.0 M, and are preferably between about 0.05 M and about 0.5 M. The excess of amine base can be greater than about 100%, but is typically between about 5% and about 25%. Aprotic solvents such as halogenated solvents are preferred (e.g., chloroform, methylene chloride and 1,2-dichloromethane), however other aprotic solvents such as ethereal solvents and hydrocarbon solvents can be suitable substitutes. Ambient temperature is normally preferred for the reaction, but temperatures between about 0° C. and about 50° can also be used.

Alternatively, the acylating agent is an activated ester $R_7C(O)$—OX', wherein —OX' is readily displaced by a primary amine. Methods of acylating an amine with activated esters are known in the art and are described in, for example, March, "Advanced Organic Chemistry—Reactions, Mechanisms and Structure", Third Edition, John Wiley & Sons, 1985, pages 371-375, and references cited therein. Many activated esters are stable enough to be isolated. N-Hydroxy succinimidyl esters, some of which are commercially available from Aldrich Chemical Co., Milwaukee, Wis., are one example of activated esters of this type. Conditions suitable for forming an amide with an acid chloride acylating agent, described in the prior paragraph, can typically be used with a stable activated ester. In contrast with acid chlorides, which require activation with tertiary amines, activated esters are reactive enough so that they form amides directly in the presence of primary amines. Therefore, the tertiary amine can be omitted from the acylation reaction when activated esters are used.

Alternatively, an activated ester is formed in situ. Formation of an activated ester in situ requires a "coupling agent", which is a reagent that replaces the hydroxyl group of a carboxyl acid with a group which is susceptible to nucleophilic displacement. Examples of coupling agents include 1,1'-carbonyldiimidazole (CDI), isobutyl chloroformate, dimethylaminopropylethyl-carbodiimide (EDC), dicyclohexyl carbodiimide (DCC). When amidating by in situ generation of an activated ester, an excess of either the carboxylic acid or amine can be used (typically a 50% excess, more typically about a 10-15% excess). However, it is more common when carrying out the present invention to use the amine compound as the limiting reagent. Generally, from about 1.0 mole to about 10 moles of coupling agent are used per mole of carboxylic acid, preferably from about 1.0 mole to about 1.5 moles of coupling agent per mole of carboxylic acid. The reaction is generally carried out in aprotic solvents, for example, halogenated solvents such as methylene chloride, dichloroethane and chloroform, ethereal solvents tetrahydrofuran, 1,4-dioxane and diethyl ether and dimethylformamide. Suitable reaction temperatures generally range from between about 0° to about 100° C., but the reaction is preferably carried out at ambient temperature.

Examples of specific conditions for carrying out the reactions described herein are provided in Examples 1 and 2.

By utilizing the enantiomer of the compound represented by Structural Formula (II) as the cyclic starting material, the enantiomer of the compounds represented by Structural Formulas (III)-(VI) and (I) can be prepared by utilizing the methods described herein. The enantiomer of the cyclic starting material represented by Structural Formula (III) can be prepared by reacting (5R)-5-phenylmorpholin-2-one with two equivalents of the aldehyde $R_1CHO$ under dehydrating conditions, as described above. The enantiomer of compounds represented by Structural Formula (III), (VII), (VIII) and (X) and methods of preparing the enantiomers of the compounds represented by Structural Formulas (II)-(VI) and (I) using procedures disclosed herein are encompassed within the present invention.

The term "enantiomer" as it used herein, and structural formulas depicting an enantiomer are meant to include the "pure" enantiomer free from its optical isomer as well as mixtures of the enantiomer and its optical isomer in which the enantiomer is present in an enantiomeric excess, e.g., at least 10%, 25%, 50%, 75%, 90%, 95%, 98%, or 99% enantiomeric excess.

With regard to the variables $R_1$-$R_5$ in Structural Formulas (I)-(IX), an "aliphatic group" is non-aromatic, consists solely of carbon and hydrogen and may optionally contain one or more units of unsaturation, e.g., double and/or triple bonds. An aliphatic group may be straight chained, branched or cyclic. When straight chained or branched, an aliphatic group typically contains between about 1 and about 30 carbon atoms, more typically between about 1 and about 24 carbon atoms. When cyclic, an aliphatic group typically contains between about 3 and about 10 carbon atoms, more typically between about 3 and about 7 carbon atoms. Aliphatic groups are preferably lower alkyl groups, which include C1-30 straight chained or branched saturated hydrocarbons, preferably C1-C24 straight chained or branched saturated hydrocarbons. Examples include methyl, ethyl, n-propyl, iso-propyl, n-butyl, sec-butyl and tert-butyl.

Aromatic groups include carbocyclic aromatic groups such as phenyl, 1-naphthyl, 2-naphthyl, 1-anthracyl and 2-anthacyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Non-aromatic heterocyclic rings are non-aromatic carbocyclic rings which include one or more heteroatoms such as nitrogen, oxygen or sulfur in the ring. The ring can be five, six, seven or eight-membered. Examples include morpholinyl, thiomorpholinyl, pyrrolidinyl, piperazinyl, piperidinyl, azetidinyl, azacycloheptyl, or N-phenylpiperazinyl.

Suitable substituents on a lower alkyl, aliphatic, aromatic, non-aromatic, heterocyclic or benzyl group are those which do not substantially interfere with the reactions described herein. "Interfering with a reaction" refers to substantially decreasing the yield (e.g., a decrease of greater than 50%) or causing a substantial amount of by-product formation (e.g., where by-products represent at least 50% of the theoretical yield). Interfering substituents can be used, provided that they are first converted to a protected form. Suitable protecting groups are known in the art and are disclosed, for example, in Greene and Wuts, "Protective Groups in Organic Synthesis", John Wiley & Sons (1991).

Suitable substituents on an alkyl, aliphatic, aromatic, non-aromatic heterocyclic ring or benzyl group include, for example, halogen (—Br, —Cl, —I and —F), —OR, —CN, —$NO_2$, —$NR_2$, —COOR, —$CONR_2$, —$SO_kR$ (k is 0, 1 or 2) and —NH—C(=NH)—$NH_2$. Each R is independently —H, an aliphatic group, a substituted aliphatic group, a benzyl group, a substituted benzyl group, an aromatic group or a substituted aromatic group, and preferably —H, a lower alkyl group, a benzylic group or a phenyl group. A substituted non-aromatic heterocyclic ring, benzylic group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted alkyl, substituted aliphatic, substituted non-aromatic heterocyclic, substituted aromatic or substituted benzyl group can have more than one substituent.

When $R_1$ is a substituted phenyl group, examples of preferred substitutents include —OCH$_2$O—, —OCH$_2$CH$_2$O—, halo, (lower alkyl)O—, lower alkyl thiol, lower dialkylamine, —OH, —O(phenyl), —OCH$_2$ (phenyl) lower alkyl, amine and lower alkyl amino.

When $R_5$ is a substituted phenyl group, examples of preferred substitutents include halo, (lower alkyl)O—, —O(phenyl) and lower alkyl.

In the structural formulas depicted herein, the remainder of the molecule or compound to which a chemical group or moiety is connected is indicated by the following symbol: "$\xi$"

For example, the corresponding symbol in Structural Formula (IX) indicates that the depicted group, which is represented by $R_6$ in Structural Formula (VIII), is connected via the benzylic carbon to the amine in Structural Formula (VIII) by a single covalent bond.

In preferred embodiments of the present invention the variables used herein are defined as follows: $R_1$ is a substituted or unsubstituted phenyl group; $R_2$ and $R_3$ are independently —H, an unsubstituted C1-C5 alkyl group or, taken together with the nitrogen atom to which they are bonded, are an unsubstituted C3-C10 non-aromatic heterocyclic ring; $R_5$ is a substituted or unsubstituted phenyl group, preferably phenyl; and $R_7$ is a C1-C30 straight chain unsubstituted aliphatic group or a C1-C30 straight chained aliphatic group substituted with one or more C1-C2 alkyl group and more preferably an unsubstituted C1-C30 straight chain alkyl or alkenyl group.

In another preferred embodiment, —NR$_2$R$_3$, taken together, is pyrrolidinyl. More preferably, —NR$_2$R$_3$, taken together, is pyrrolidinyl and $R_5$ is phenyl in compounds comprising $R_2$, $R_3$ and $R_5$. Even more preferably, in compounds comprising $R_1$, $R_2$, $R_3$ and $R_5$, $R_1$ is a substituted or unsubstituted phenyl group (preferably phenyl substituted in the meta/para positions with —OCH$_2$O—, —OCH$_2$CH$_2$O— or in the para position with halo, lower alkyl thiol, —OH, —O(phenyl), —O—CH$_2$(phenyl), lower alkyl, amino, lower alkyl amine, lower dialkyl amino, or —O(lower alkyl), —NR$_2$R$_3$, taken together, is pyrrolindinyl and $R_5$ is phenyl.

In another preferred embodiment, —NR$_2$R$_3$, taken together, is piperidyl. More preferably, —NR$_2$R$_3$, taken together, is piperidyl and $R_5$ is phenyl in compounds comprising $R_2$, $R_3$ and $R_5$. Even more preferably, in compounds comprising $R_1$, $R_2$, $R_3$ and $R_5$, $R_1$ is a substituted or unsubstituted phenyl group (preferably phenyl substituted in the meta/para positions with —OCH$_2$O—, —OCH$_2$CH$_2$O— or in the para position with halo, lower alkyl thiol, —OH, —O(phenyl), —OCH$_2$-(phenyl), —OCH$_2$ (phenyl), lower alkyl, amino, lower alkyl amino, lower dialkyl amino, or —O(lower alkyl), —NR$_2$R$_3$, taken together, is piperidyl and $R_5$ is phenyl.

Examples of ceramide-like compounds which can be prepared by the methods of the present invention are represented by Structural Formula (XI):

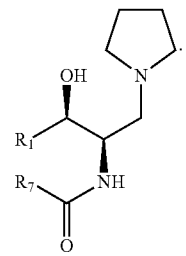

(XI)

$R_1$ is phenyl substituted in the meta/para positions with —OCH$_2$O— or —OCH$_2$CH$_2$O— or in the para position with halo, CH$_3$O—, CH$_3$CH$_2$O—, CH$_3$CH$_2$CH$_2$O—, CH$_3$(CH$_3$)CHO—, CH$_3$—, CH$_3$CH$_2$—, CH$_3$CH$_2$CH$_2$—, CH$_3$(CH$_3$)CH—, —OH or —OCH$_2$(phenyl); and $R_7$ is CH$_3$(CH$_2$)$_n$— or CH$_3$(CH$_2$)$_{n-2}$CH=CH—, wherein n is an integer from 0 to about 30. Preferably, n is 7, 8, 9, 10, 11, 12, 13, 14, 15, 16, 17, 18, 19, 20, 21, 22, 23 or 24. More preferably, $R_1$ is phenyl substituted meta/para with —OCH$_2$CH$_2$O—.

Compounds of this invention which possess a sufficiently acidic, a sufficiently basic, or both functional groups, and accordingly can react with any of a number of inorganic bases, and inorganic and organic acids, to form a salt. Thus, the present invention also includes salts of the intermediates represented by Structural Formulas (VII), (VIII) and (X). Physiologically acceptable salts are preferred. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The entire teachings of the publications cited in this application are incorporated herein by reference.

EXEMPLIFICATION

Example 1

Small Scale Preparation of Ceramid-Like Compounds

Intermediate 1

(1R,3S,5S,8aS)-1,3-Bis-(2',3'-dihydro-benzo[1,4]dioxin-6'-yl)-5-phenyl-tetrahydro-oxazolo[4,3-c][1,4]oxazin-8-one

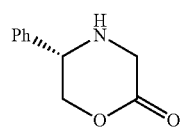

+

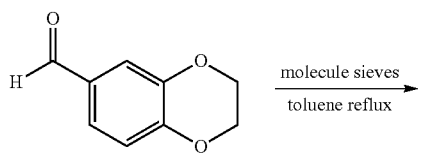

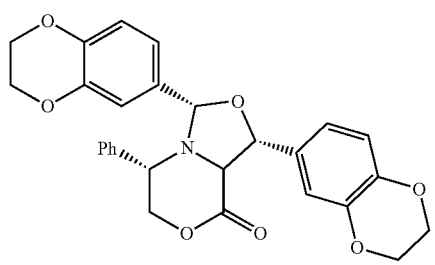

To a stirred solution of (5S)-5-phenylmorpholim-2-one (2.00 g, 11.3 mmol) (prepared as in: Dellaria, J. F.: Santarsiero, B. D. *J. Org. Chem.*, 1989, 54, 3916) and 1,4-benzodioxan-6-carboxaldehyde (5.56 g, 33.9 mmol) in toluene (125 mL) was added 4 Å molecular sieves (approximately 20 mL). The mixture was heated at reflux for 72 hours, filtered free of sieves and concentrated. The resulting amber gum was flash chromatographed over silica (diethyl ether/hexane) to furnish a pale yellow solid. This material was further purified by trituration with diethyl ether to afford 1.89 g (34%) product as a fluffy white solid: $^1$H NMR (CDCl$_3$) δ 7.31-7.17 (m, 5H), 6.95-6.79 (m, 5H), 5.32-5.27 (m, 2H), 4.43-4.28 (m, 2H), 4.24 (s, 4H), 4.18 (m, 4H), 4.16-4.08 (m, 2H) ppm.

Intermediate 2

(2S,3R,1"S)-3-(2',3'-Dihydro-benzo[1,4]dioxin-6'-yl)-3-hydroxy-2-(2"-hydroxy-1"-phenyl-ethyl-amino)-1-pyrrolidin-1-yl-propan-1-one

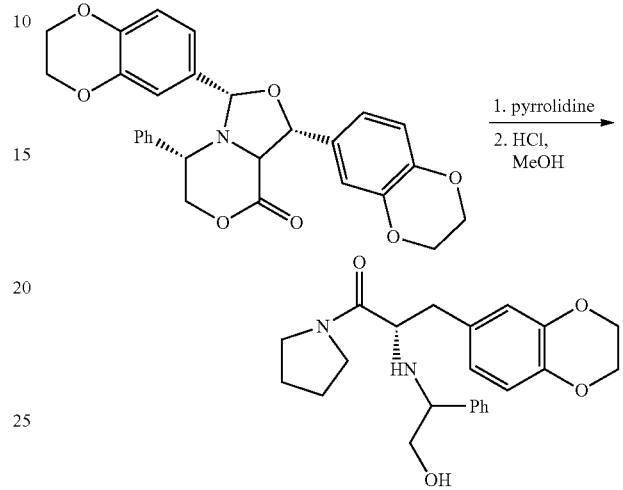

To a stirred solution of Intermediate 1 (1.80 g, 3.69 mmol) in chloroform (20 mL) was added pyrrolidine (2.0 mL, 24 mmol). The solution was stirred overnight and then concentrated. The resulting colorless tacky foam was taken up in methanol (16 mL) and 1 N hydrochloric acid (4 mL). The mixture was refluxed for 1 hour, treated with additional 1 N hydrochloric acid (2 mL) and refluxed for another 2 hours. The reaction solution was concentrated and the resulting residue partitioned between ethyl acetate and aqueous sodium bicarbonate solution. The organic layer was dried (sodium sulfate) and concentrated. The resulting pale yellow gum was purified by flash chromatography over silica gel (methylene chloride/2 N methanolic ammonia) to afford 1.40 g (92%) of Intermediate 2 as a colorless foamy solid: $^1$H NMR (CDCl$_3$) δ 7.31-7.13 (m, 5H), 6.93-6.70 (m, 3H), 4.47 (d, J=8.5, 1H), 4.18 (s, 4H), 3.82 (t, J=5.9, 1H), 3.74 (d, J=6.0, 2H), 3.06 (d, J=8.5, 1H), 3.06-2.97 (m, 2.92-2.83 (m, 1H), 1.97-1.87 (m, 1H), 1.45-1.15 (m, 4H) ppm.

Intermediate 3

(1R,2R,1"S)-1-(2',3'-Dihydro-benzo[1,4]dioxin-6'-yl)-2-(2"-hydroxy-1"-phenyl-ethylamino)-3-pyrrolidin-1-yl-propan-1-ol

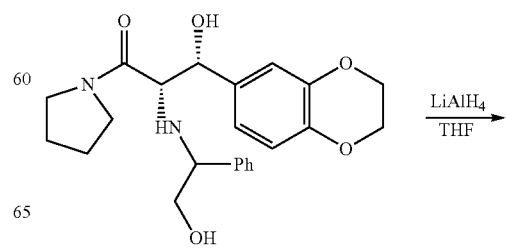

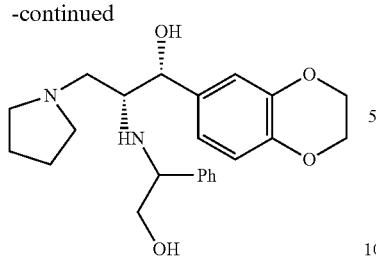

To a stirred solution of Intermediate 2 (1.38 g, 3.35 mmol) in tetrahydrofuran (30 mL) was added lithium aluminum hydride (0.26 g, 6.9 mmol). The foamy suspension was stirred overnight and then quenched with the addition (dropwise until frothing ceases) of 1 N aqueous sodium hydroxide (13 mL). The mixture was diluted with water and extracted with ethyl acetate. The organic layer was dried (sodium sulfate) and concentrated to afford a colorless gum. Flash chromatography over silica gel (methylene chloride/2 N methanolic ammonia) afforded 0.94 g (70%) of product as a colorless tacky foam: $^1$H NMR (CDCl$_3$) δ 7.36-7.17 (m, 5H), 6.88-6.74 (m, 3H), 4.42 (d, J=5.4, 1H), 4.26 (s, 4H), 3.79-3.69 (m, 1H), 3.64-3.56 (m, 1H), 3.55-3.45 (m, 1H), 3.00-2.90 (m, 1H), 2.67-2.57 (m, 1H), 2.43-2.32 (m, 4H), 2.25-2.15 (m, 1H), 1.75-1.65 (m, 4H) ppm.

Intermediate 4

(1R,2R)-2-Amino-1-(2',3'-dihydro-benzo[1,4]dioxin-6'-yl)-3-pyrrolidin-1-yl-propan-1-ol

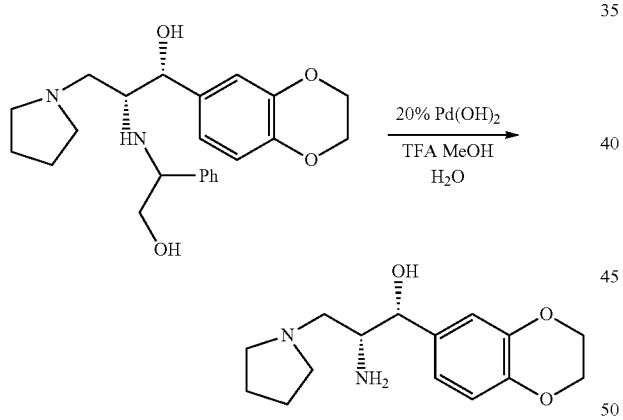

In a high pressure reaction bomb equipped with a mechanical stirrer was loaded a solution of Intermediate 3 (0.91 g, 2.28 mmol) in 10:1 methanol/water (22 mL), trifluoroacetic acid (0.18 mL, 2.3 mmol) and 20% palladium hydroxide on carbon (Perlman's catalyst; 0.91 g). The reactor was evacuated and backfilled with argon three times and then evacuated and refilled with hydrogen (100 psi). The reaction was stirred for 2 days and then evacuated and flushed with nitrogen. The reaction solution was filtered through Celite and concentrated. The resulting gray-green gum was flash chromatographed over silica gel (methylene chloride/2 N methanolic ammonia) to afford 0.165 g (26%) of product as a near colorless gum: $^1$H NMR (CDCl$_3$) δ 6.89-6.76 (m, 3H), 4.54 (d, J=3.7, 1H), 4.25 (s, 4H), 3.43 (s, 1H), 3.14-3.07 (m, 1H), 2.68-2.41 (m, 6H), 1.82-1.71 (m, 4H) ppm.

Compound 5

(1R,2R)-Hexadecanoic acid [2-(2',3'-dihydro-benzo[1,4]dioxin-6'-yl)-2-hydroxy-1-pyrrolidin-1-ylm-ethyl-ethyl]-amide

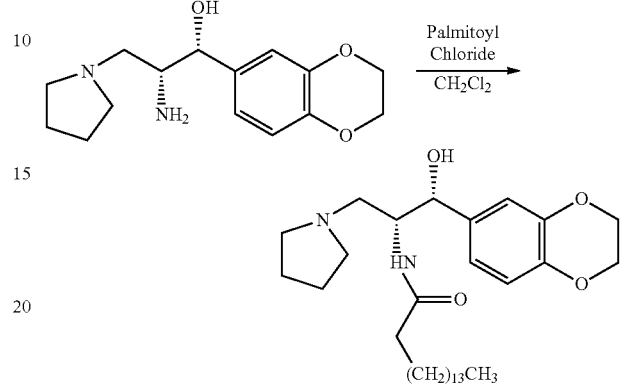

To a stirred solution of Intermediate 4 (0.165 g, 0.593 mmol) in methylene chloride (8 mL) was added palmitoyl chloride (0.18 g, 0.59 mmol) followed by N,N-diisopropylethylamine (0.11 mL, 0.65 mmol). The solution was stirred for 2 hours and then concentrated. The residue was partitioned between ethyl acetate and aqueous sodium bicarbonate solution. The organic layer was dried (sodium sulfate) and concentrated. The resulting off-white solid was flash chromatographed over silica gel (methylene chloride/2 N methanolic ammonia) to afford 0.174 g (57%) of product as a white solid. Comparisons by $^1$H NMR spectroscopy and analytical chiral HPLC (column: Chirex (S)-VAL and (R)-NE, 4.6×250 mm; eluant: 0.5% trifluoroacetic acid in 67:31:2 hexane/methylene chloride/ethanol; flow: 1 mL/min; detection 280 nM) demonstrate that this material was identical to a sample of the same compound prepared by the method of Polt, et al. (*J. Org. Chem.*, 1998, 63, 8837). Enantiomeric excess was determined to be 99.6%. Total contamination from the two possible diastereomers is determined to be 0.2%. $^1$H NMR (CDCl$_3$) δ 6.88-6.73 (m, 3H), 5.84 (d, J=7.3, 1H), 4.90 (d, J=3.8, 1H), 4.24 (s, 4H), 4.22-4.15 (m, 1H), 2.86-2.72 (m, 2H), 2.72-2.55 (m, 4H), 2.10 (t, J=7.5, 2H), 1.82-1.74 (m, 4H), 1.58-1.46 (m, 2H), 1.32-1.16 (m, 24H), 0.88 (t, J=6.7, 3H) ppm.

Example 2

Large Scale Preparation of Ceramide-Like Compounds (5S)-5-Phenylmorpholin-2-One

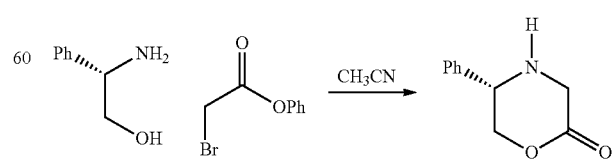

A solution of S-(+)-Phenyl glycinol (Aldrich, 10.17 g, 78.12 mmol) and Diisopropylethylamine (Aldrich, 34 mL, 195 mmol, 2.5 equivalents) was prepared in CH$_3$CN (200 mL). This solution was added to phenyl-α-bromoacetate (18.48 g, 85.9 mnol, 1.1 equivalents) dissolved in CH$_3$CN (50 mL) under nitrogen dropwise over 2 hours. The resulting solution was stirred under nitrogen for 16-20 hours. The solvent was removed by rotoevaporation keeping the bath temperature at below 25° C. To the oil was added ethyl acetate (120 mL) and the mixture was stirred for 15 minutes. The resulting white precipitate was filtered off and the solid washed with ethyl acetate (25 mL). The filtrate was rotoevaporated to an oil keeping the bath temperature below 25° C. After drying under vacuum for 0.5 hours, the oil was dissolved in CH$_2$Cl$_2$ (17 mL) and loaded onto a silica gel column (60 g packed with 10% ethyl acetate/hexanes. The upper byproduct spots were eluted with 10% ethyl acetate/hexanes and the product was eluted with 50% ethyl acetate/hexanes-100% ethyl acetate. The fractions containing the product were rotoevaporated to an oil keeping the bath temperature below 25° C. This oil was dissolved in ethyl acetate (12 mL) and hexanes (60 mL) was added slowly in an ice bath to precipitate the product. The resulting precipitate was filtered. The white to yellow solid was vacuum dried. The (5S)-5-phenylmorpholin-2-one obtained (7.4 g, 41.8 mmol, 53%) was used directly in the next step.

Intermediate 1

(1R,3S,5S,8aS)-1,3-Bis-(2',3'-dihydro-benzo[1,4]dioxin-6'-yl)-5-phenyl-tetrahydro-oxazolo[4,3-c][1,4]oxazin-8-one

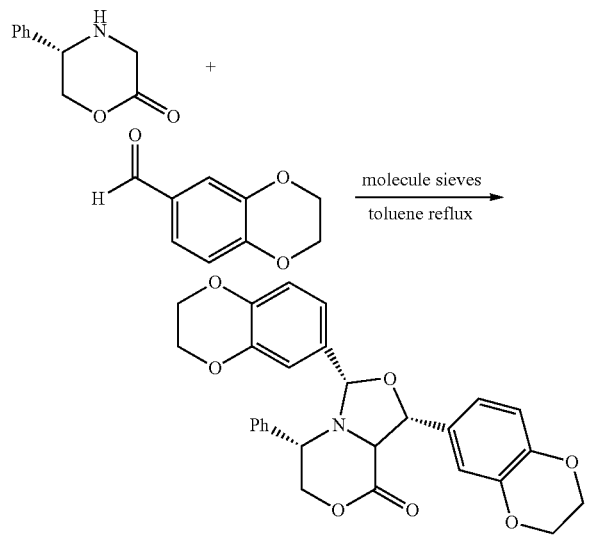

(5S)-5-Phenylmorpholin-2-one (7.4 g, 41.8 mmol) and benzodioxolane-6-carboxaldehyde (Aldrich or Alfa Aesar, 20.56 g, 125.2 mmol, 3.0 equivalents) was dissolved in toluene (180 mL). The solution was placed in a soxhlet extractor apparatus filled with 4 Å molecular sieves (ca 30 g). The solution was refluxed under nitrogen for 2-3 days. After cooling to room temperature, the solvent was removed by rotoevaporation and the oil was dissolved in ethyl acetate (200 mL). A solution of sodium bisulfite (Aldrich, 50 g) in water (100 mL) was added and the two phase mixture was stirred at room temperature for 1 hour. The resulting white solid was filtered off and washed with ethyl acetate. The filtrate was placed in a separatory funnel and the layers separated. The organic layer was washed with water (100 mL) and saturated sodium chloride solution (100 mL). The dried (Na$_2$SO$_4$) solution was filtered and rotoevaporated to a yellow-red foamy oil (23.11 g). After drying under vacuum for 1 hour, diethyl ether (350 ml) was added and the mixture was stirred at room temperature for 16-20 hours. The resulting white-yellow solid was filtered. The solid was dried under vacuum. The cycloadduct was obtained in 46% yield (9.34 g).

Intermediate 2

(2S,3R,1"S)-3-(2',3'-Dihydro-benzo[1,4]dioxin-6'-yl)-3-hydroxy-2-(2"-hydroxy-1"-phenyl-ethyl-amino)-1-pyrrolidin-1-yl-propan-1-one

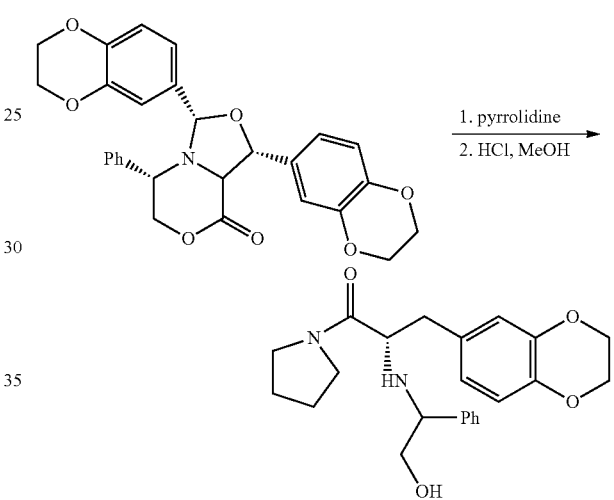

To the cycloadduct (Intermediate 1, 6.7 g, 13.74 mmol) dissolved in methylene chloride (40 mL) was added pyrrolidine (Aldrich, 5.7 mL, 68.7 mmol, 5 equivalents). The solution was stirred under nitrogen at room temperature for 16-18 hours. The solvent was rotoevaporated to yield a yellow foamy oil which was vacuum dried for 0.5 hours. The crude was dissolved in methanol (115 mL) and a 1 M aqueous HCl solution (115 mL) was added. The solution was refluxed for 4 hours. After cooling to room temperature, the methanol was removed by rotoevaporation. Ethyl acetate (60 mL) was added and the two phase system was stirred at room temperature for 5-15 minutes. The two layers were separated and the organic layer was extracted with 1 M HCL (30 mL). The combined aqueous layers were washed two times with ethyl acetate (60, 30 mL). A saturated sodium bicarbonate solution (150 mL) was added to the aqueous layer slowly. The product was extracted three times with ethyl acetate (60 mL) from the basic (pH=8-9) aqueous layer. The combined organic layers containing the product were washed with a saturated sodium chloride solution (30 mL). After drying with Na$_2$SO$_4$ the solution was filtered and rotoevaporated to yield a yellow solid. Intermediate 2 was obtained in 93% yield (5.26 g).

Intermediate 3

(1R,2R,1″S)-1-(2',3'-Dihydro-benzo[1,4]dioxin-6'-yl)-2-(2″-hydroxy-1″-phenyl-ethylamino)-3-pyrrolidin-1-yl-propan-1-ol

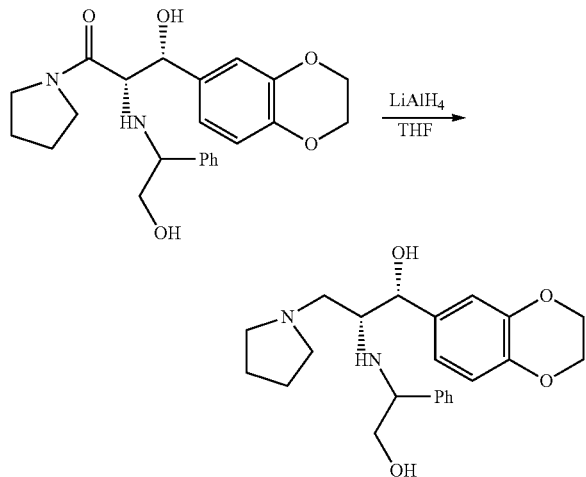

To a 3-neck flask equipped with a dropping funnel and condenser was added LiAlH$_4$ (Aldrich, 1.2 g, 31.7 mmol, 2.5 equivalents) and anhydrous THF (20 mL) under nitrogen. A solution of Intermediate 2 (5.23 g, 12.68 mmol) in anhydrous THF (75 mL) was added dropwise to the reaction over 15-30 minutes. The reaction was refluxed under nitrogen for 9 hours. The reaction was cooled in an ice bath and a 1M NaOH solution was carefully added dropwise. After stirring at room temperature for 15 minutes, water (50 mL) and ethyl acetate (75 mL) was added. The layers were separated and the aqueous layer was extracted twice with ethyl acetate (75 mL). The combined organic layers were washed with saturated sodium chloride solution (25 mL). After drying with Na$_2$SO$_4$ the solution was filtered and rotoevaporated to yield a colorless to yellow foamy oil. Intermediate 3 was obtained in 99% yield (5.3 g).

Intermediate 4

(1R,2R)-2-Amino-1-(2',3'-dihydro-benzo[1,4]dioxin-6'-yl)-3-pyrrolidin-1-yl-propan-1-ol

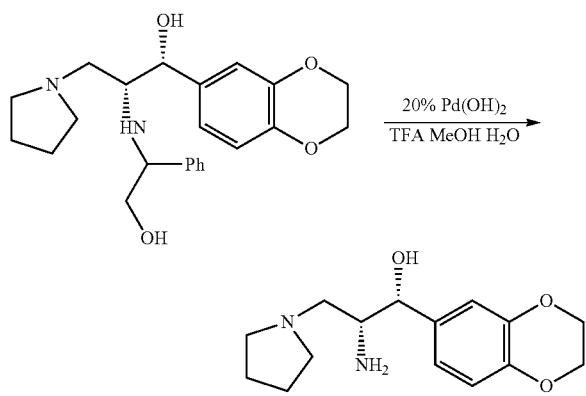

Intermediate 3 (5.3 g, 13.3 mmol) was dissolved in methanol (60 mL). Water (6 mL) and trifluoroacetic acid (2.05 mL, 26.6 mmol, 2 equivalents) were added. After being placed under nitrogen, 20% Palladium hydroxide on carbon (Pearlman's catalysis, Lancaster or Aldrich, 5.3 g) was added. The mixture was placed in a Parr Pressure Reactor Apparatus with glass insert. The apparatus was placed under nitrogen and then under hydrogen pressure 110-120 psi. The mixture was stirred for 2-3 days at room temperature under hydrogen pressure 100-120 psi. The reaction was placed under nitrogen and filtered through a pad of celite. The celite pad was washed with methanol (100 mL) and water (100 mL). The methanol was removed by rotoevaporation. The aqueous layer was washed with ethyl acetate three times (100, 50, 50 mL). A 10 M NaOH solution (10 mL) was added to the aqueous layer (pH=12-14). The product was extracted from the aqueous layer three times with methylene chloride (100, 100, 50 mL). The combined organic layers were dried with Na$_2$SO$_4$, filtered and rotoevaporated to a colorless oil. The foamy oil was vacuum dried for 2 h. Intermediate 4 was obtained in 90% yield (3.34 g).

Compound 5

(1R,2R)-Hexadecanoic acid [2-(2',3'-dihydro-benzo[1,4]dioxin-6'-yl)-2-hydroxy-1-pyrrolidin-1-ylmethyl-ethyl]amide

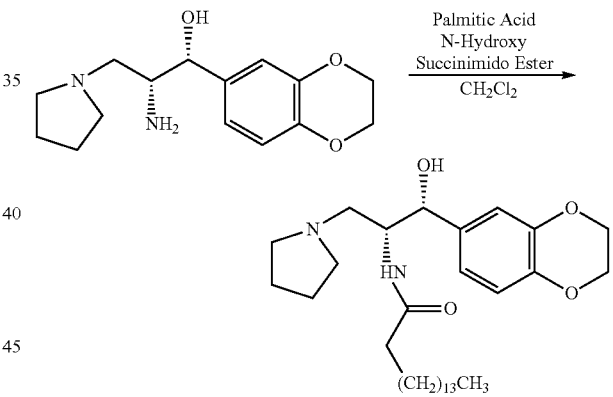

To a solution of Intermediate 4 (3.34 g, 12.0 mmol) in methylene chloride (50 mL) was added a solution of palmitic acid N-hydroxylsuccinimide ester (Sigma, 4.24 g, 12.0 mmol) over 15-30 minutes under nitrogen at room temperature. The solution was stirred at room temperature for 18-20 hours. To the reaction was added methylene chloride (50 mL) and a 1 M NaOH solution (25 mL). The two phase system was stirred at room temperature for 15-30 min. Water (25 mL) was added and the layers were separated. The aqueous layer was back extracted with methylene chloride (25 mL). The combined organic layers were washed twice with water (25 mL) and once with a saturated sodium chloride solution (25 mL). The organic layer was dried with Na$_2$SO$_4$, filtered and rotoevaporated to a light yellow oil. The crude was recrystallized from hexane (50 mL). The white solid (5.46 g) obtained was separated on silica gel (300 g) with 2% methanol:methylene chloride-4% methanol:methylene chloride-4% 2 M ammonium in methanol:methylene chloride. The white solid obtained was recrystallized form hexanes (70 mL). Compound 5 was obtained in 66% yield (4.18 g). Analytical chiral HPLC (column: Chirex (S)-VAL and (R)-NE, 4.6×250 mm; eluant: 0.5% trifluoroacetic acid in 67:31:2 hexane/methylene chloride/ ethanol; flow: 1 mL/min; detection: 280 nM) showed this material to be 98.98% pure with 0.89% of a diastereoisomer and 0.14% of the enantiomer.

Example 3

Alternative Large Scale Preparation of Ceramide-Like Compounds (5S)-5-Phenylmorpholin-2-one HCl salt A solution of phenyl bromoacetate (Aldrich, 862.17 g, 4.0 moles, 1.1 equivalents) in acetonitrile (reagent grade, 1500 ml) was cooled in an ice bath (internal temperature below 5° C.). To this was added a cold slurry (internal temperature below 5° C.) of S-(+)-2-phenyl glycinol (Aldrich, 500 g, 3.65 moles, 1 equivalent) and diisopropylethylamine (DIPEA) (Aldrich, 1587 ml, 9.11 moles, 2.5 equivalents) in acetonitrile (2900 ml) in portions while keeping the internal temperature below 10° C. The mixture was stirred at this temperature for 30 minutes before the ice bath was removed and the mixture was allowed to stir at room temperature for an additional 4 hours. The solvent was removed in vacuo while maintaining the bath temperature at 25° C. The mixture was coevaporated with ethyl acetate (2×500 ml) to produce a light yellow viscous oil. To the reaction mixture, ethyl acetate (4500 ml) was added and the flask was immersed in an ice bath with agitation. The mixture was allowed to cool below 8° C. The solid was filtered and washed with ethyl acetate (3×250 ml). The solution was cooled to below 5° C. Dry HCl gas was passed slowly into the solution while maintaining the internal temperature below 15° C. until the pH was below 2 (wet pH paper). The mixture was allowed to stir at this temperature and pH for an additional 20 minutes before the solid was suction filtered. The solid was washed with ethyl acetate (3×200 ml) and dried under high vacuum for about 20 hours. The yield was 412 g (53%). $^1$H NMR was consistent with the (5S)-5-phenylmorpholin-2-one HCl salt.

Intermediate 1

(1R,3S,5S,8aS)-1,3-Bis-(2',3'-dihydro-benzo[1,4] dioxin-6'-yl)-5-phenyl-tetrahydro-oxazolo[4,3-c][1, 4]oxazin-8-one To a stirred suspension of (5S)-5-phenylmorpholin-2-one HCl salt (381 g, 1 equivalent) in 15% ethyl acetate in toluene (2270 ml) was added a solution of sodium bicarbonate (1.1 equivalents) in water (2000 ml). The resulting biphasic solution was stirred at room temperature for about 1 hour. The organic layer was transferred to a flask containing 1,4-benzodioxan-6-carboxaldehyde. The flask was then equipped with a Dean-Stark unit, a condenser and a nitrogen inlet. The mixture was heated at reflux with agitation while about 650 ml solvent (mixture of ethyl acetate and toluene) was collected via Dean-Stark unit. The resulting yellow-red solution was allowed reflux for about 64 hours, under nitrogen while the water formed during the reaction was collected in the Dean-Stark unit. Most of the solvent was then removed via distillation at atmospheric pressure through Dean-Stark unit. The residual solvent was then removed by coevaporation with heptane (500 ml) and tert-butylmethyl ether (2×725 ml) to produce a yellow semi solid product. The semi solid product was dissolved in ethyl acetate (3400 ml). A solution of sodium bisulfate (920 g) in water (1500 ml) was added and the mixture was allowed to stir at room temperature for about 1 hour. The solid that was formed was removed by filtration and washed with ethyl acetate (3×400 ml). The filtrate was washed with water (1450 ml), 5% brine solution (1450 ml) and dried over MgSO$_4$ (100 g). The solvent was removed in vacuo to afford a yellow solid. To this was added tert-butylmethyl ether (2900 ml) and the suspension was stirred at room temperature for 20 to 22 hours. The yellow solid was suction filtered, washed with tert-butylmethyl ether (2×600 ml) and dried under high vacuum at room temperature for about 22 hours. The yield was 400.5 g (58%). $^1$H NMR and TLC were consistent with Intermediate 1.

Intermediate 2

2S,3R,1"S)-3-(2',3'-Dihydro-benzo[1,4]dioxin-6'-yl)-3-hydroxy-2-(2"-hydroxy-1"-phenyl-ethylamino)-1-pyrrolidin-1-yl-propan-1-one A solution of Intermediate 1 (312 g, 0.64 moles), pyrrolidine (267 ml, 3.2 moles, 5 equivalents) and tetrahydrofuran (1350 ml) was heated at reflux for 4.5 hours under nitrogen atmosphere. The solvent and excess pyrrolidine were removed in vacuo to produce the crude intermediate as an orange viscous oil. The oil was dissolved in methanol (3000 ml) and 1M hydrochloric acid solution (3000 ml). The resulting solution was heated at reflux for about 7 hours. The solvent was then removed in vacuo to afford a mixture of an oil and water. To this ethyl acetate (2000 ml) was added and the aqueous layer was separated. The organic layer was extracted with aqueous 1M HCl (1000 ml). The aqueous layers were combined and washed with ethyl acetate (2000 ml). The aqueous layer was cooled in an ice bath. The pH of the aqueous layer was adjusted to about 9 (pH paper) with 10 M aqueous NaOH (525 ml). The aqueous layer was extracted with ethyl acetate (3000 ml). The organic layer was washed with 5% brine solution (1000 ml) and dried (Na$_2$SO$_4$). The solvent was removed in vacuo to produce a yellow viscous oil. The yield was 213.4 g, 81%. $^1$H NMR was consistent with Intermediate 2.

Intermediate 3

1R,2R,1"S)-1-(2',3'-Dihydro-benzo[1,4]dioxin-6'-yl)-2-(2"-hydroxy-1"-phenyl-ethylamino)-3-pyrrolidin-1-yl-propan-1-ol To a slurry of LiAlH$_4$ (50.7 g, 1.34 moles, 2.6 equivalents) in tetrahydrofuran (700 ml) was added a solution of intermediate 2 (213.34 g, 0.517 moles) in tetrahydrofuran (2000 ml) slowly with agitation at room temperature. The mixture was refluxed for about 4 hours. TLC analysis (10% methanol in methylene chloride, v/v) indicated consumption of the starting material. The reaction mixture was cooled in an ice bath (below 5° C.) and water (135 ml) was added very slowly while keeping the internal temperature less than or equal to 10° C. To this was then added a 15% aqueous NaOH solution (70 ml) followed by water (200 ml). The reaction mixture was allowed to warm to room temperature while the agitation was continued. Methylene chloride (1000 ml) was then added to the mixture and the salts were filtered through a pad of celite. The salts were washed with methylene chloride (2×500 ml). The filtrates were combined and the solvent was removed in vacuo to produce a yellow oil. The oil was dissolved in 1M aqueous HCl (1500 ml) and washed with ethyl acetate (3×500 ml). The aqueous layer was cooled in an ice bath to below 5° C. and the pH of the aqueous layer was adjusted to 12 to 13 with a 10 M aqueous NaOH solution (220 ml) keeping the internal temperature at less than or equal to 10° C. The mixture was allowed to warm to room temperature. The aqueous layer was extracted with methylene chloride (2×500 ml). The organic layers were combined and washed with brine solution (500 ml), dried ($Na_2SO_4$) and the solvent was removed in vacuo to afford a yellow viscous oil. The yield was 186.4 g (88.5%). $^1$H NMR was consistent with Intermediate 3.

Intermediate 4 dioxalate salt (1R,2R)-2-Amino-1-(2',3'-dihydro-benzo[1,4]dioxin-6'-yl)-3-pyrrolidin-1-yl-propan-1-ol dioxalate salt A suspension of Intermediate 3 (358 g, 0.90 moles), ethanol (1500 ml), 1M HCl solution (1500 ml) and 10% Pd(OH)$_2$ (32 g, 20 weight %) were hydrogenated at about 50 psi for about 36 h at room temperature. The mixture was filtered through a Cuono filter. The Cuono filter was washed with 10% ethanol in water (500 ml). The filtrates were combined and ethanol was removed in vacuo. The aqueous layer was extracted with ethyl acetate (3×600 ml). The organic layer was extracted with 1M HCl aqueous (700 ml). The aqueous layers were combined and cooled in an ice bath (0 about 5° C.). The pH of the aqueous layer was adjusted to about 12 (pH paper) with 10 M aqueous NaOH solution (490 ml) keeping the internal temperature below 10° C. The aqueous layer was allowed to warm to room temperature. The aqueous layer was extracted with methylene chloride (2×1500 ml, 1×750 ml). The combined organic layers were dried over MgSO$_4$ and the solvent was removed in vacuo to afford a yellow viscous oil. The crude weight was 214.3 g (86%). $^1$H NMR was consistent with Intermediate 4.

A solution of oxalic acid (152.4 g, 1.693 moles, 2.2 equivalents) in methylisobutyl ketone (2300 ml) was added slowly with stirring to a solution of Intermediate 4 (214.3 g, 0.77 moles, 1 equivalent) in methylisobutyl ketone (800 ml) at room temperature. The resulting mixture was stirred at room temperature for about 2.5 hours. The solid was filtered, and triturated with acetone (2000 ml) at room temperature for about 16 hours. The solid was filtered, washed with acetone (3×100 ml) and dried under high vacuum to produce an off-white solid. The yield was 312.5 g (89%). $^1$H NMR was consistent with Intermediate 4 dioxalate salt.

Compound 5

(1R,2R)-Hexadecanoic acid [2-(2',3'-dihydro-benzo[1,4]dioxin-6'-yl)-2-hydroxy-1-pyrrolidin-1-ylmethyl-ethyl]-amide To a cold solution (about 5° C.) of Intermediate 4 dioxalate salt (507 g, 1.11 moles) in water (10 L) was added a 10 M aqueous NaOH solution (500 ml) with stirring while keeping the internal temperature below 10° C. The solution was allowed to warm to room temperature while the pH of the solution was maintained at about 14 (pH paper). The aqueous layer was extracted with methylene chloride (3×6000 ml). The organic layers were combined, washed with water (2000 ml), dried (MgSO$_4$) and the solvent was removed in vacuo to afford a yellow viscous oil, Intermediate 4. The yield was 302 g (98%). $^1$H NMR was consistent with Intermediate 4.

A solution of palmitic acid NHS-ester (Sigma, 382.5 g, 1.01 equivalents) in methylene chloride (2500 ml) was added to a solution of intermediate 4 (302 g) in methylene chloride (1500 ml) at room temperature over a period of 1.25 hours under a nitrogen atmosphere. The mixture was allowed to stir at room temperature for about 18 hours. A solution of 1M aqueous NaOH (2425 ml) was added and the mixture was stirred at room temperature for about 3 hours. The organic layer was separated and the aqueous layer was extracted with methylene chloride (800 ml). The organic layers were combined, washed with a 1M NaOH solution (3×1500 ml) and water (1500 ml). The organic layer was dried over MgSO$_4$ and the solvent was removed in vacuo to afford a semi solid. The semi-solid was coevaporated with heptane (3×100 ml). The crude product was transferred to a 12 L three-necked RB flask and heptane (7500 ml) was added. The mixture was heated at reflux with stirring under a nitrogen atmosphere. The solution was slowly cooled to about 55° C. (internal temperature) and poured into another flask. The solution was stirred at room temperature for 24 hours under a nitrogen atmosphere. The off white solid was filtered, washed with heptane (2×500 ml) and dried under high vacuum for 24 hours. The solid (397 g) was transferred to a 12 L RB flask and 30% ethyl acetate in heptane (8000 ml) was added. The resulting mixture was heated at reflux for 30 minutes with stirring. The solution was cooled to about 55° C. (internal temperature) and poured into another flask. The stirring was continued at room temperature under a nitrogen atmosphere for about 24 hours. The solid was filtered, washed with heptane (2×100 ml) and dried under high vacuum to afford an off white solid. The yield was 324 g (58%). $^1$H NMR and TLC were consistent with Compound 5. mp 96.1° C. HPLC analysis: chiral purity 99.7%, chemical purity 99.7%. Anal. Calcd for $C_{31}R_{52}N_2O_4$: C, 72.05; H, 10.14; N, 5.42. Found C, 72.03; H, 10.19; N, 5.42.

Example 4

Preparation of Compounds 6-8

N-hydroxysuccinimide esters of fatty acids were prepared by the method of Lapidot, Y. Rappoport, S. and Wolman, *Y. Journal of Lipid Research* 8, 1967 or as described below:

Octanoic Acid N-Hydroxysuccinimide Ester

N-hydroxysuccinimide (Aldrich, 20.0 g, 173 mmol) and triethyl amine (29 mL, 208 mmol) were dissolved in methylene chloride in an ice bath under nitrogen. Octanoyl chloride (Aldrich, 35 mL, 205 mmol) was added dropwise over 0.5 hours. The ice bath was removed and the solution with a white solid was stirred for 1 hour at room temperature. The white solid was removed by filtration and the filtrate was washed with water (100 mL) and saturated aqueous sodium bicarbonate (100 mL). The organic layer was dried with sodium sulfate, filtered and heptane (100 mL) was added. The solution was rotoevaporated to remove most of the methylene chloride and leave a colorless to white flaky precipitate in heptane. The precipitate was filtered and washed with heptane. After drying, Octanoic acid N-hydroxysuccinimide ester was obtained in 84% yield (35.4 g).: $^1$H NMR (CDCl$_3$) 2.84 (br s, 4H), 2.60 (t, J=7.48 Hz, 2H), 1.78-1.71 (m, 2H), 1.42-1.26 (m, 8H), 0.88 (t, J=6.7 Hz, 311) ppm.

Compound 6

(1R,2R)-Octanoic acid [2-(2',3'-dihydro-benzo[1,4]dioxin-6'-yl)-2-hydroxy-1-pyrrolidin-1-ylmethyl-ethyl]-amide

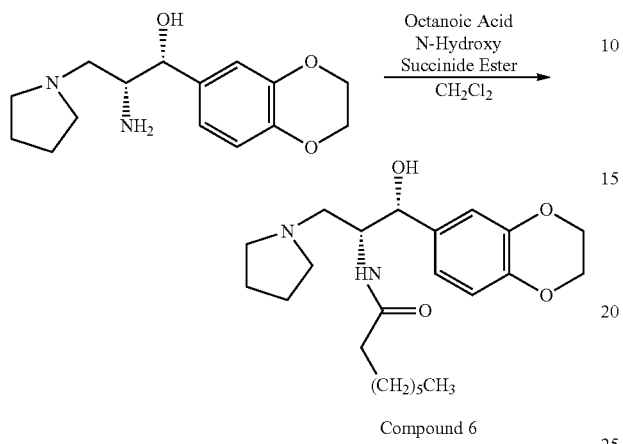

Compound 6

To Intermediate 5 (22.36 g, 80.33 mmol) dissolved in anhydrous methylene chloride (300 mL) was added a solution of octanoic acid N-hydroxysuccinimide ester (19.4 g, 80.39 mmol) dissolved in anhydrous methylene chloride (150 mL) over 15-30 minutes under nitrogen at room temperature. The solution was stirred at room temperature for 18-20 hours. To the reaction was added 1M aqueous NaOH solution (200 mL). The two phase system was stirred at room temperature for 45 minutes. The layers were separated and the combined organic layers were washed twice with 1M NaOH (2×200 mL) and twice with water (2×100 mL). The organic layer was dried with sodium sulfate, filtered and rotoevaporated to a yellow oil. Most of the crude material was dissolved in 5% ethyl acetate in heptane (1 L) at reflux. After cooling to 40° C., the hazy solution was separated from the yellow oil by decanting the solution into a new flask. The first flask was rinsed twice with 5% ethyl acetate in heptane (2×250 mL) by the same process (reflux and cooling to 40° C. and decanting the solution from the oil). The combined solution was heated to reflux and allowed to cool to room temperature over 4 hours. The resulting white solid was filtered and washed with 5% ethyl acetate in heptane (100 mL) and heptane (100 mL). The white solid (13.9 g) was dried under vacuum for 16-24 hours. This solid was mostly dissolved in 5% ethyl acetate in heptane (800 mL) at reflux. After cooling to 50° C., the hazy solution was separated from the yellow oil by decanting the solution into a new flask. The first flask was rinsed with 5% ethyl acetate in heptane (100 mL) by the same process (reflux and cooling to 50° C. and decanting the solution from the oil). The combined solution was heated to reflux and allowed to cool to room temperature over 4 hours. The resulting white solid was filtered and washed with 5% ethyl acetate/heptane (50 mL) and heptane (50 mL). After drying at room temperature under vacuum for 2-3 days, Compound 6 was obtained in 39% yield (12.57 g). Analytical chiral HPLC (column: Chirex (S)-VAL and (R)—NE, 4.6×250 mm) showed this material to be 99.9% the desired R,R isomer. Analytical HPLC showed this material to be 99.6% pure. mp 87-88° C. $^1$H NMR (CDCl$_3$) δ 6.86-6.73 (m, 3H), 5.84 (d, J=7.3 Hz, 1H), 4.91 (d, J=3.4 Hz, 1H), 4.25 (s, 4H), 4.24-4.18 (m, 1H), 2.85-2.75 (m, 2H), 2.69-2.62 (m, 4H), 2.10 (t, J=7.3 Hz, 2H), 1.55-1.45 (m, 2H), 1.70-1.85 (m, 4H), 1.30-1.15 (m, 8H), 0.87 (t, J=6.9 Hz, 3H) ppm.

Compound 7

(1R,2R)-Nonanoic acid [2-(2',3'-dihydro-benzo[1,4]dioxin-6'-yl)-2-hydroxy-1-pyrrolidin-1-ylmethyl-ethyl]-amide

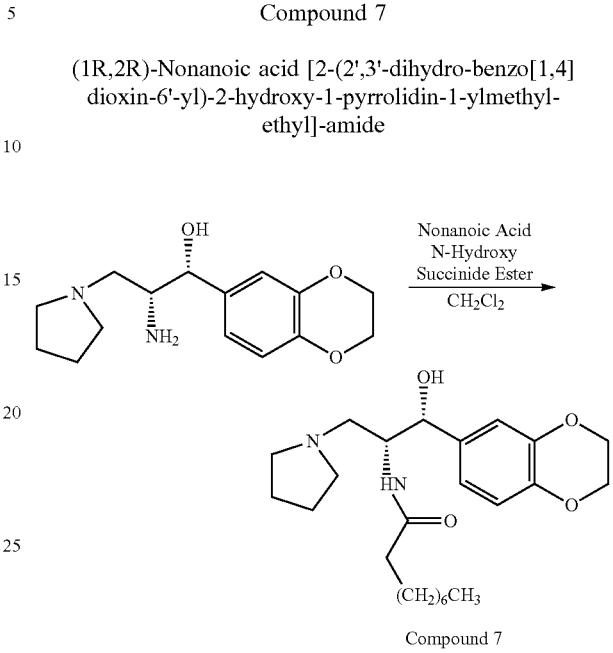

Compound 7

This compound was prepared by the method described for Compound 6 using Nonanoic acid N-hydroxysuccinimide ester. Analytical HPLC showed this material to be 98.4% pure. mp 74-75° C. $^1$H NMR (CDCl$_3$) δ 6.86-6.76 (m, 3H), 5.83 (d, J=7.3 Hz, 1H), 4.90 (d, J=3.3 Hz, 1H), 4.24 (s, 4H), 4.24-4.18 (m, 1H), 2.85-2.75 (m, 2H), 2.69-2.62 (m, 4H), 2.10 (t, J=7.3 Hz, 2H), 1.55-1.45 (m, 2H), 1.70-1.85 (m, 4H), 1.30-1.15 (m, 10H), 0.87 (t, J=6.9 Hz, 3H) ppm.

Compound 8

(1R,2R)-Decanoic[2-(2',3'-dihydro-benzo[1,4]dioxin-6'-yl)-2-hydroxy-1-pyrrolidin-1-ylmethyl-ethyl]-amide

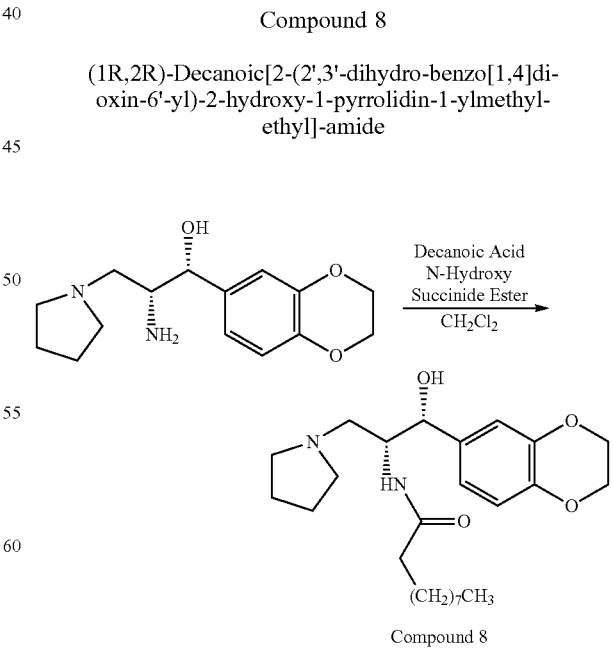

Compound 8

This compound was prepared by the method described for Compound 6 using decanoic acid N-hydroxysuccinimide ester. Analytical HPLC showed this material to be 99.3% pure. mp 97.5-98.5° C. $^1$H NMR (CDCl$_3$) δ 6.86-6.76 (m, 3H), 5.83 (d, J=7.5 Hz, 1H), 4.90 (d, J=3.4 Hz, 1H), 4.24 (s, 4H), 4.24-4.18 (m, 1H), 2.85-2.75 (m, 2.69-2.62 (m, 4H), 2.10 (t, J=7.5 Hz, 2H), 1.55-1.45 (m, 2H), 1.70-1.85 (m, 4H), 1.30-1.15 (m, 12H), 0.87 (t, J=6.8 Hz, 3H) ppm.

Example 5

Preparation of Compound 13

Intermediate 9

(1R,3S,5S,8aS)-1,3-Bis-(4-benzyloxy-phenyl)-5-phenyl-tetrahydro-oxazolo[4,3-c][1,4]oxazin-8-one

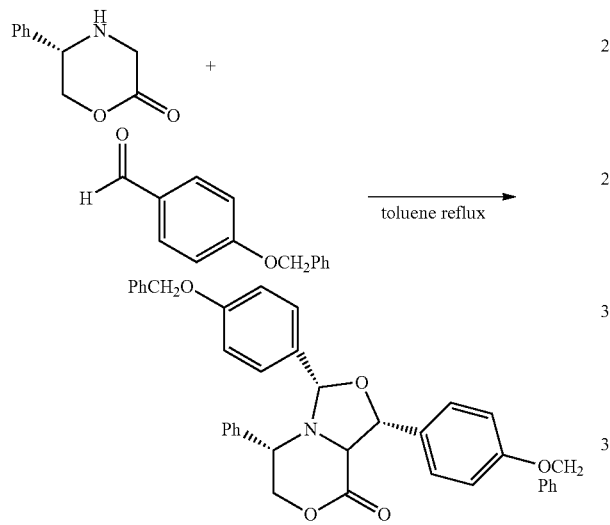

The (5S)-5-phenylmorpholin-2-one HCl salt (57.45, 268.9 mmol) was stirred with ethyl acetate (500 mL) and saturated aqueous sodium bicarbonate (250 mL) for 30 minutes, until the biphasic solution was clear. The phases were separated, and the aqueous layer was extracted with ethyl acetate (2×250 mL). The combined organic phases were washed with saturated sodium chloride solution (250 mL). The organic layer was dried with sodium sulfate, filtered, concentrated to an oil, and dried under vacuum for 60 minutes. The 5-(S)-phenyl morpholin-2-one was obtained in a 86% yield (40.98 g, 231.3 mmol).

The 5-(S)-phenyl morpholin-2-one (40.98 g, 231.3 mmol) and 4-benzyloxybenzaldehyde (Aldrich, 147.3 g, 694 mmol, 3.0 equivalents) was dissolved in toluene (750 mL). The reaction was fitted with a Dean Stark Trap and a reflux condenser. The solution was refluxed under nitrogen for 2 days. After cooling to room temperature, the solvent was removed by rotoevaporation and the oil was dissolved in ethyl acetate (500 mL). A solution of sodium bisulfite (Aldrich, 125 g) dissolved in water (250 mL) was added and the two phase mixture was stirred at room temperature for 3 hours. The resulting white solid was filtered off and washed with ethyl acetate. The filtrate was placed in a separatory funnel and the layers separated. The organic layer was washed with water (250 mL), saturated aqueous sodium chloride solution (250 mL) and then dried (sodium sulfate) filtered and rotoevaporated to a foamy oil (144 g). After drying under vacuum for 1 hour, tert-butyl methyl ether (1450 mL) was added and the mixture was stirred at room temperature for 5 hours. The resulting white-yellow solid was filtered. The solid was dried under vacuum. Intermediate 9 was obtained in 27% yield (41.64 g, 71.46 mmol). $^1$H NMR (CDCl$_3$) δ 7.5-6.8 (m, 23H), 5.0 and 5.1 (2 s, 4H), 4.5-4.3 (m, 2H), 4.2-4.1 (m, 2H) ppm.

Intermediate 10

(2S,3R,1"S)-3-(4-Benzyloxy-phenyl)-3-hydroxy-2-(2"-hydroxy-1"-phenyl-ethylamino)-1-pyrrolidin-1-yl-propan-1-one

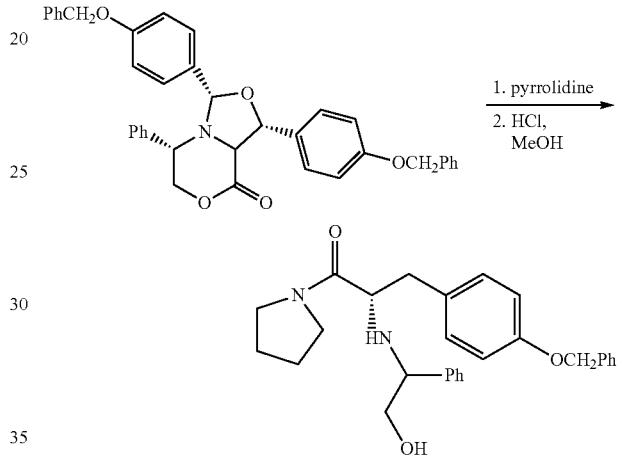

To Intermediate 9 (45.1 g, 77.4 mmol) dissolved in tetrahydrofuran (250 mL) was added pyrrolidine (Aldrich 33 mL, 395 mmol, 5.1 equivalents). The solution was stirred capped under nitrogen at room temperature for 16-18 hours. The solvent was rotoevaporated to yield a yellow foamy oil which was vacuum dried for 0.5 hours. The crude was dissolved in methanol (220 mL) and a 1M aqueous HCl solution (220 mL) was added. The solution was refluxed for 4 hours. After cooling to room temperature, the methanol was removed by rotoevaporation. To the resulting oil was slowly added 10 M aqueous NaOH (22 mL to adjust the pH to 14). The product was extracted three times with methylene chloride (300, 100, 100 mL) from the basic aqueous layer. After drying with sodium sulfate the combined organic layer was filtered and rotoevaporated to yield a yellow-orange foamy solid. Tert-butyl methyl ether (300 mL) was added and the mixture was stirred at room temperature for 7 hours. The resulting white-yellow solid was filtered, washed with tert-butyl methyl ether (50 mL) and vacuum dried. Intermediate 10 was obtained in 83% yield (29.77 g). $^1$H NMR (CDCl$_3$) δ 7.4-7.2 (m, 12H), 6.9-6.8 (m, 2H), 5.05 (AB quartet, 2H), 4.47 (d, J=8.5, 1H), 3.9-3.3 (m, 3H), 3.05 (d, J=8.5, 1H), 3.0-2.8 (m, 2H), 2.3-2.2 (m, 1H), 1.85-1.7 (m, 1H), 1.45-1.15 (m, 4H) ppm.

Intermediate 11

(1R,2R,1"S)-1-(4-Benzyloxy-phenyl)-2-(2"-hydroxy-1"-phenyl-ethylamino)-3-pyrrolidin-1-yl-propan-1-ol

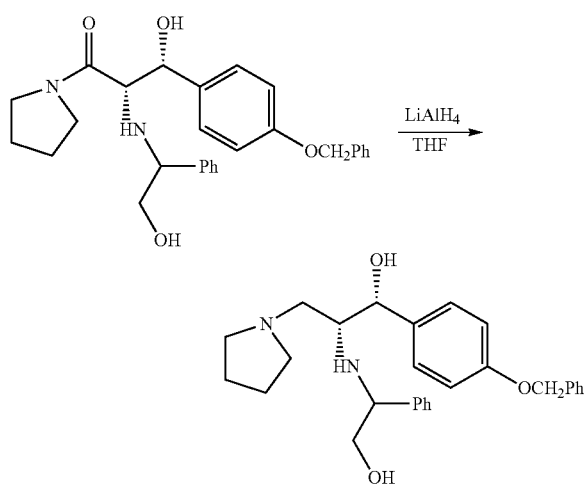

In a 3-neck flask with dropping funnel and condenser under nitrogen was added LiAlH$_4$ (Aldrich, 6.3 g, 166 mmol, 2.57 equivalents) and anhydrous tetrahydrofuran (75 mL). A solution of Intermediate 10 (29.7 g, 64.48 mmol) in anhydrous tetrahydrofuran (300 mL) was added dropwise to the reaction over 15-30 minutes. The reaction was refluxed under nitrogen for 9 hours. The reaction was cooled in an ice bath and water (7.0 mL) was very carefully added drop by drop (vigorous exothermic reaction with hydrogen being given off). A 5% aqueous NaOH solution (7.0 mL) was added dropwise followed by water (21 mL). Halfway through the final water addition a large amount of a white solid formed. It was broken up by the addition of methylene chloride (250 mL). After stirring at room temperature for 15 minutes, the mixture was filtered through a celite plug (17 cm in diameter by 1 cm in height). The precipitate was washed with methylene chloride (2×250 mL). The filtrate was rotoevaporated to an oil. The oil was dissolved in 1M aqueous HCl (300 mL). This aqueous layer was washed with tert-butyl methyl ether (2×200 mL). After cooling in an ice bath, 10 M aqueous NaOH (35 mL) was carefully added to the aqueous layer (final pH=14). The product was extracted three times with methylene chloride (300 mL, 200 mL and 100 mL). After drying with sodium sulfate, the solution was filtered and rotoevaporated to yield a white solid. After drying, the Intermediate 11 was obtained in 94% yield (26.9 g). $^1$H NMR (CDCl$_3$) δ 7.46-7.115 (m, 12H), 6.98-6.96 (m, 2H), 5.08 (s, 2H), 4.49 (d, J=4.7, 1H), 3.70-3.65 (m, 1H), 3.60-3.55 (m, 1H), 3.54-3.45 (m, 1H), 3.00-2.90 (m, 1H), 2.7-2.6 (m, 1H), 2.36 (br s, 4H), 2.15-2.05 (m, 1H), 1.70 (br s, 4H) ppm.

Intermediate 12

(1R,2R)-2-Amino-1-(4-benzyloxy-phenyl)-3-pyrrolidin-1-yl-propan-1-ol Hydrogen chloride salt

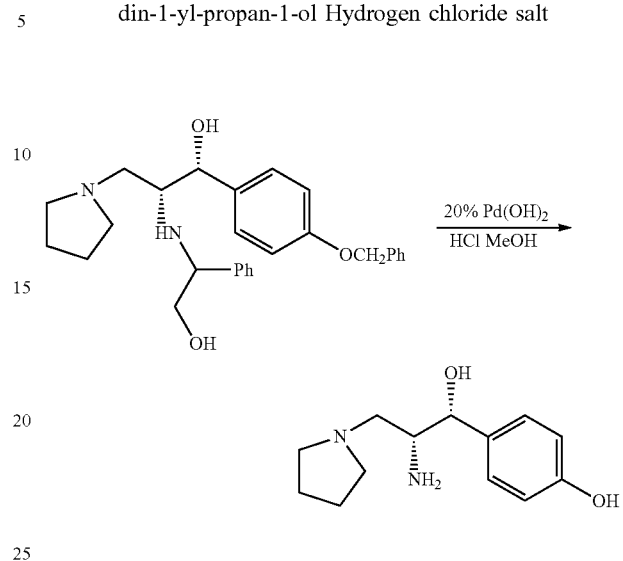

Intermediate 11 (26.9 g, 60.24 mmol) was dissolved in methanol (400 mL) and 1M aqueous HCl (130 mL) was added. After being placed under nitrogen, 20% palladium hydroxide on carbon (Pearlman's catalysis, Aldrich, 10.8 g) was added. The reaction was placed under nitrogen and then under hydrogen by evacuation and filling to a balloon. The mixture was stirred for 48 hours at room temperature under a hydrogen balloon. The reaction was placed under nitrogen and filtered through a pad of celite. The celite pad was washed with 10% water in methanol (250 mL) and water (50 mL). The solvent was removed by rotoevaporation and coevaporation with toluene (3×100 mL). The foamy solid was dissolved in isopropanol (300 mL) at reflux. The solution was cooled to room temperature and tert-butyl methyl ether (550 mL) was added. After stirring at room temperature for 2 hours, the white solid was filtered and washed with tert-butyl methyl ether. After drying, Intermediate 12 was obtained in ca 99% yield (18 g). $^1$H NMR (DMSO-d6) δ 9.68 (br s, 1H), 8.53 (br s, 2H) 7.24 (d, J=8.55 Hz, 2H), 6.80 (d, J=8.55 Hz, 2H), 4.72 (d, J=7.0 Hz, 1H), 3.8-3.6 (m, 2H), 3.4-3.6 (m, 3H), 3.0-3.2 (m, 2H), 2.7-2.5 (br s, 1H), 2.0-1.7 (br s, 4H) ppm.

Compound 13

(1R,2R)-Hexadecanoic acid [2-(4-benzyloxy-phenyl)-2-hydroxy-1-pyrrolidin-1-ylmethyl-ethyl]-amide

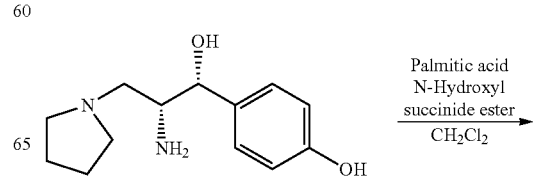

Palmitic acid
N-Hydroxyl
succinide ester
CH$_2$Cl$_2$

-continued

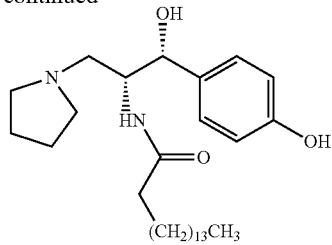

To Intermediate 12 (16.17 g 49.36 mmol) suspended in tetrahydrofuran (500 mL) was added triethylamine (28 mL, 4 equivalents). A solution of Palmitic acid N-hydroxysuccinimide ester (Sigma, 19.2 g, 54.29 mmol) dissolved in tetrahydrofuran (125 mL) was added over 30 minutes under nitrogen at room temperature. The solution was stirred at room temperature for 18-20 hours. The white precipitate was removed by filtration and the filtrate was rotoevaporated to a foamy off-white solid (35.5 g). The crude material was dissolved in methylene chloride (500 mL) and washed with water (100 mL) and saturated aqueous sodium carbonate solution (100 mL). After drying with sodium sulfate, the solution was filtered and rotoevaporated to yield a off-white foamy solid (24.75 g). This material was recrystallized from 40% ethyl acetate in heptane (500 mL, hot filtration). Compound 13 was obtained in 61% yield (14.45 g) Analytical chiral HPLC showed this material to be 99.7% the desired R,R isomer. Analytical HPLC showed this material to be 99.6% pure. mp 95-97° C. $^1$H NMR (CDCl$_3$) δ 7.15 (d, J=8.5 Hz, 2H), 6.70 (d, J=8.5 Hz, 2H), 6.0 (d, J=7.3, 1H), 4.96 (d, J=3.8, 1H), 4.3-4.2 (m, 1H), 2.9-2.7 (m, 2H), 2.65-2.55 (m, 4H), 2.10 (t, J=7.5, 2H), 1.75 (br s, 4H), 1.58-1.46 (m, 2H), 1.32-1.16 (m, 24H), 0.9 (t, J=6.7, 3H) ppm.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing an amine compound represented by the following structural formula:

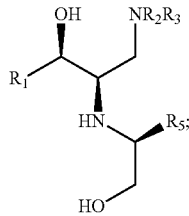

wherein:
R$_1$ is a substituted or unsubstituted aromatic group;
R$_2$ and R$_3$ are independently —H, a substituted or unsubstituted aliphatic group or, taken together with the nitrogen atom to which they are bonded, are a substituted or unsubstituted non-aromatic heterocyclic ring; and
R$_5$ is a substituted or unsubstituted aromatic group,
said method comprising the step of reacting a cyclic starting material with HNR$_2$R$_3$, said cyclic starting material being represented by the following structural formula:

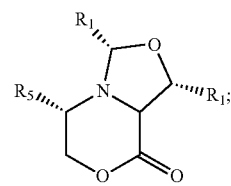

thereby forming an intermediate represented by the following structural formula:

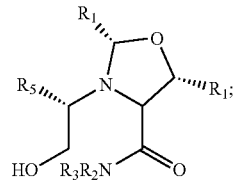

hydrolyzing the amino acetal group of the intermediate, thereby forming the acyclic compound represented by the following structural formula:

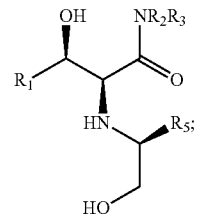

and reacting the acyclic compound with an amide reducing agent, thereby forming the amine compound.

2. The method of claim 1 wherein the amide reducing agent is lithium aluminum hydride.

3. The method of claim 1 wherein the amide reducing agent is borane tetrahydrofuran.

* * * * *